United States Patent
Bloom et al.

(10) Patent No.: US 7,666,835 B2
(45) Date of Patent: Feb. 23, 2010

(54) OXYNTOMODULIN FOR PREVENTING OR TREATING EXCESS WEIGHT

(75) Inventors: Stephen Robert Bloom, London (GB); Mohammad Ali Ghatei, Middlesex (GB); Caroline Jane Small, Ascot (GB); Catherine Louise Dakin, Lower Kingswood (GB)

(73) Assignee: Imperial Innovations Limited, London (GB)

( * ) Notice: Subject to any disclaimer, the term of this patent is extended or adjusted under 35 U.S.C. 154(b) by 0 days.

(21) Appl. No.: 10/488,341

(22) PCT Filed: Sep. 9, 2002

(86) PCT No.: PCT/GB02/04082

§ 371 (c)(1), (2), (4) Date: Nov. 8, 2004

(87) PCT Pub. No.: WO03/022304

PCT Pub. Date: Mar. 20, 2003

(65) Prior Publication Data

US 2005/0070469 A1    Mar. 31, 2005

(30) Foreign Application Priority Data

Sep. 7, 2001    (GB)    ................. 0121709.0

(51) Int. Cl.
A61K 38/17    (2006.01)
(52) U.S. Cl. ........................................ 514/12
(58) Field of Classification Search .................. None
See application file for complete search history.

(56) References Cited

U.S. PATENT DOCUMENTS

| | | | |
|---|---|---|---|
| 4,220,653 A * | 9/1980 | Vivino | 514/400 |
| 4,698,327 A * | 10/1987 | Nagarajan et al. | 514/8 |
| 5,432,156 A * | 7/1995 | Matsuno et al. | 514/12 |
| 5,858,975 A * | 1/1999 | Yano et al. | 514/12 |
| 6,191,102 B1 | 2/2001 | DiMarchi et al. | 514/2 |
| 6,583,111 B1 | 6/2003 | DiMarchi et al. | |
| 6,586,403 B1 * | 7/2003 | Mathison et al. | 514/18 |
| 7,459,432 B2 | 12/2008 | Cowley et al. | |
| 2001/0011071 A1 * | 8/2001 | Knudsen et al. | 514/12 |
| 2001/0046956 A1 * | 11/2001 | Hadcock | 514/2 |
| 2002/0156010 A1 * | 10/2002 | Lustig | 514/12 |
| 2004/0018975 A1 | 1/2004 | DiMarchi et al. | |
| 2005/0070469 A1 * | 3/2005 | Bloom et al. | 514/12 |
| 2005/0176630 A1 | 8/2005 | Cowley et al. | |
| 2006/0014678 A1 | 1/2006 | Cowley et al. | |
| 2006/0189522 A1 | 8/2006 | Bloom et al. | |
| 2008/0064636 A1 | 3/2008 | Bloom et al. | |
| 2009/0181885 A1 | 7/2009 | Bloom | |
| 2009/0209461 A1 | 8/2009 | Cowley et al. | |

FOREIGN PATENT DOCUMENTS

| | | |
|---|---|---|
| EP | 0 619 332 A | 10/1994 |
| EP | 0 795 562 A1 | 9/1997 |
| WO | 03/026591 | 4/2003 |
| WO | 03/057235 | 7/2003 |
| WO | 2004/062685 | 7/2004 |
| WO | 2006/134340 | 12/2006 |
| WO | 2007/100535 | 9/2007 |
| WO | 2008/003947 | 1/2008 |
| WO | 2008/071972 | 6/2008 |

OTHER PUBLICATIONS

H. E. Bays. Obesity Res. (2004) 12(8), pp. 1197-1211.*
"The Wonders of Weight Loss" American Fitness. Jan./Feb. 2006, p. 18.*
R. Parker. Internet document <http://www.futurepundit.com/archives/002946.html> Aug. 17, 2005, 4 pages; accessed Aug. 29, 2006.*
J. Rudinger. In: Peptide Hormones, JA Parsons, Ed. (1976) 1-7.*
D. Voet and J.G. Voet. Biochemistry, 2nd Edition.(1995), pp. 235-241.*
D.E. Smilek, et al. Proc. Natl. Acad. Sci. USA (1991) 88, pp. 9633-9637.*
W.S. Messer, "Vasopressin and Oxytocin", web document updated Apr. 3, 2000; <http://www.neurosci.pharm.utoledo.edu/MBC3320/vasopressin.htm>; 5 pages.*
M.F. Wikosz and R.H. Bogner. US Pharmacist (2003) 28(4), 15 pages.*
S. Senel and A.A. Hincal. J. Cont. Rel. (2001) 72, pp. 133-144.*
B.T. Schjoldager, et al. Eur. J. Clin. Invest. (1988) 18(5), pp. 499-503.*
"Oxyntomodulin" internet document <http://www.glucagon.com/oxyntomodulin.htm> Mar. 3, 2001, 2 pages; accessed Aug. 30, 2006.*
Dakin et al., "Repeated ICV Administration of Oxyntomodulin Causes a Greater Reduction in Body Weight Gain Than in Pair-Fed Rats," Am. J. Physiol. Endocrinol. Metab., 283:E1173-E1177, 2002.
Dakin et al., "Oxyntomodulin Inhibits Food Intake in the Rat," Endocrinology, 142(10):4244-4250, 2001.
Uesaka et al., "Glucagon-Like Peptide Isolated from the Eel Intestine: Effects on Atrial Beating," J. Exp. Biol., 204:3019-3026, 2001.
International Search Report for PCT/GB02/04082, mailed Jan. 23, 2003.
Assuncao, "Weight gain management in patients with schizophrenia during treatment with olanzapine in association with nizatidine", Rev. Bras. Psiquiatr., 28(4):270-276 (2006).
Garrow, "Does cimetidine cause weight loss?", BMJ., 306(6885):1084 (1993).
Rasmussen, "Cimetidine suspension as adjuvant to energy restricted diet in treating obesity", BMJ., 306(6885):1093-1096 (1993).

(Continued)

Primary Examiner—Andrew D Kosar
(74) Attorney, Agent, or Firm—Lando & Anastasi, LLP

(57) ABSTRACT

Compositions and methods for use in the prevention or treatment of excess weight in a mammal have been developed. The compositions comprise oxyntomodulin which is shown to reduce food intake.

18 Claims, 19 Drawing Sheets

OTHER PUBLICATIONS

Stoa-Birketvedt, "Cimetidine reduces weight and improves metabolic control in overweight patients with Type 2 diabetes", *International Journal of Obesity Relat. Metab. Disord.*, 22(11):1041-1045 (1998).

Stoa-Birketvedt, "Effect of cimetidine suspension on appetite and weight in overweight subjects", *BMJ.*, 306(6885):1091-1093 (1993).

Stoa-Birketvedt, "$H_2$-receptor antagonist reduces food intake and weight gain in rats by non-gastric acid secretory mechanisms", *Scandinavian Physiological Society*, 161(4):489-494 (1997).

Walan and Ström, "Metabolic consequences of reduced gastric acidity", Scand. J. Gastroenterol. Suppl., 111:24-30 (1985).

Andersen & Rasmussen "Cimetidine and obesity: Conflicting evidence" Intl. J. Obesity 23:550 (1999).

Bagger et al. "Nasal bioavailability of peptide T in rabbits: Absorption enhancement by sodium glycocholate and glycofurol" Eur. J. Pharm. Sci. 14:69-74 (2001).

Kawana et al. "Nasal immunization of mice with peptide having a cross-neutralization epitope on minor capsid protein L2 of human papillomavirus type 16 elicit systemic and mucosal antibodies" Vaccine 19:1496-1502 (2001).

Tani et al. "Oxyntomodulin and related peptides control somatostatin secretion in RIN T3 cells" Biochim. Biophys. Acta 1095:249-254 (1991).

Tzotsas et al. "Use of somatostatin analogues in obesity" Drugs 68:1963-1973 (2008).

Wynne et al. "Subcutaneous oxyntomodulin reduces body weight in overweight and obese subjects" Diabetes 54:2390-2395 (2005).

Dakin et al. "Novel actions of oxyntomodulin in the central nervous system" J. Endocrinol., abstract supplement (19th Joint Meeting of the British Endocrine Societies, with the European Federation of Endocrine Societies—Mar. 13-16, 2000) 164(suppl):P181 (Mar. 2000).

P01275 (gi45644939): "Glucagon precursor", GenBank Record dated Jan. 23, 2007, (GenBank [online] Bethesda, MD USA: United States National Library of Medicine, retrieved on Jun. 9, 2007, retrieved from internet using <URL:http://www.ncbi.nlm.nih.gov/entrez/viewer.fcgi?db=protein&val=45644939>, GenBank Accession No. P01275 (gi45644939).

P01275 (gi121484): "Glucagon precursor", GenBank Record dated Aug. 20, 2001, (GenBank [online] Bethesda, MD USA: United States National Library of Medicine, retrieved on Jun. 9, 2007, retrieved from internet using <URL:http://www.ncbi.nlm.nih.gov/entrez/viewer.fcgi?121484:)OLD09:43184>, GenBank Accession No. P01275 (gi121484).

P01273 (gi1346151): "Glucagon precursor", GenBank Record dated Jul. 10, 2007, (GenBank [online] Bethesda, MD USA: United States National Library of Medicine, retrieved on Jun. 9, 2007, retrieved from internet using <URL:http://www.ncbi.nlm.nih.gov/entrez/viewer.fcgi?db=protein&val=1346151>, GenBank Accession No. P01273 (gi1346151).

P01275: "GLUC_HUMAN", ExPASy [online] Swiss Institute of Bioinformatics (SIB), Gasteiger E., Gattiker A., Hoogland C., Ivanyi I., Appel R.D., Bairoch A. ExPASy: the proteomics server for in-depth protein knowledge and analysis Nucleic Acids Res. 31:3784-3788(2003), retrieved on May 27, 2005, retrieved from internet using <URL:http://www.au.expasy.org/cgi-bin/sprot-ft-details.pl?P01275@PEPTIDE@53@89>, ExPASy Accession No. P01275.

P01272 (gi121479): "Glucagon precursor", GenBank Record dated Aug. 21, 2007, (GenBank [online] Bethesda, MD USA: United States National Library of Medicine, retrieved on Jun. 9, 2007, retrieved from internet using <URL:http://www.ncbi.nlm.nih.gov/entrez/viewer.fcgi?db=protein&val=121479>, GenBank Accession No. P01272 (gi121479).

P06883 (gi121496): "Glucagon precursor", GenBank Record dated Jul. 10, 2007, (GenBank [online] Bethesda, MD USA: United States National Library of Medicine, retrieved on Jun. 9, 2007, retrieved from internet using <URL:http://www.ncbi.nlm.nih.gov/entrez/viewer.fcgi?db=protein&val=121496>, GenBank Accession No. P06883 (gi121496).

Bowie et al., "Deciphering the Message in Protein Sequences: Tolerance to Amino Acid Substitutions", Science, vol. 247, pp. 1306-1310, Mar. 16, 1990.

"Novel Actions of Oxyntomodulin in the Central Nervous System", CL Dakin et al., Dept. of Endocrinology & Metabolism, Imperial College School Medicine, Hammersmith Hospital, Du Cane Road, London. W12 ONN, Journal of Endocrinology, Mar. 2000, vol. 164 Supplement (Abstract #181).

"Novel Actions of Oxyntomodulin in the Central Nervous System", CL Dakin et al., Dept. of Endocrinology & Metabolism, Imperial College School Medicine, Hammersmith Hospital, Du Cane Road, London. W12 ONN. UK presented at 19th Joint Meeting of the British Endocrine Societies, with the European Federation of Endocrine Societies, Mar. 13-16, 2000.

\* cited by examiner

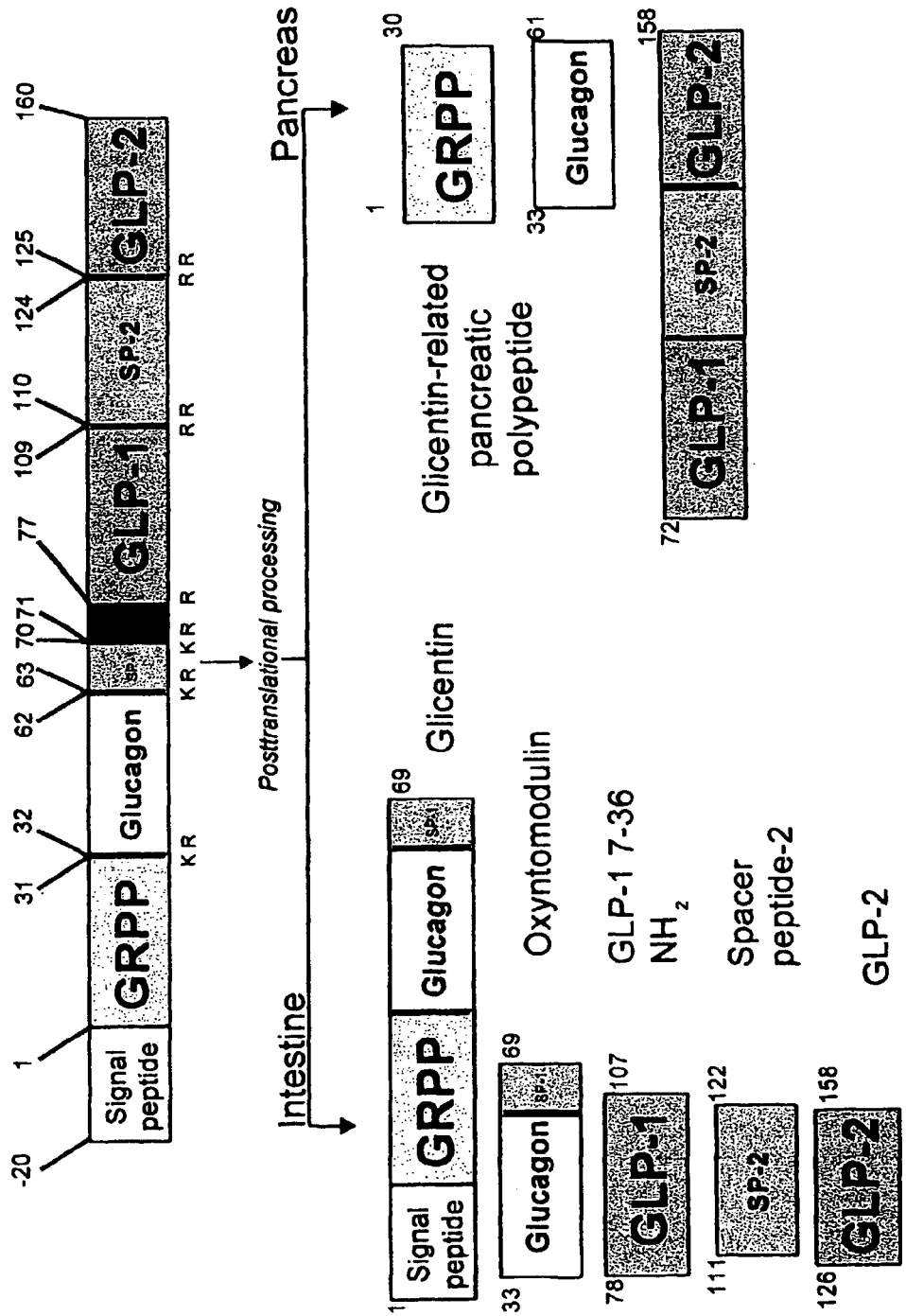
Figure A

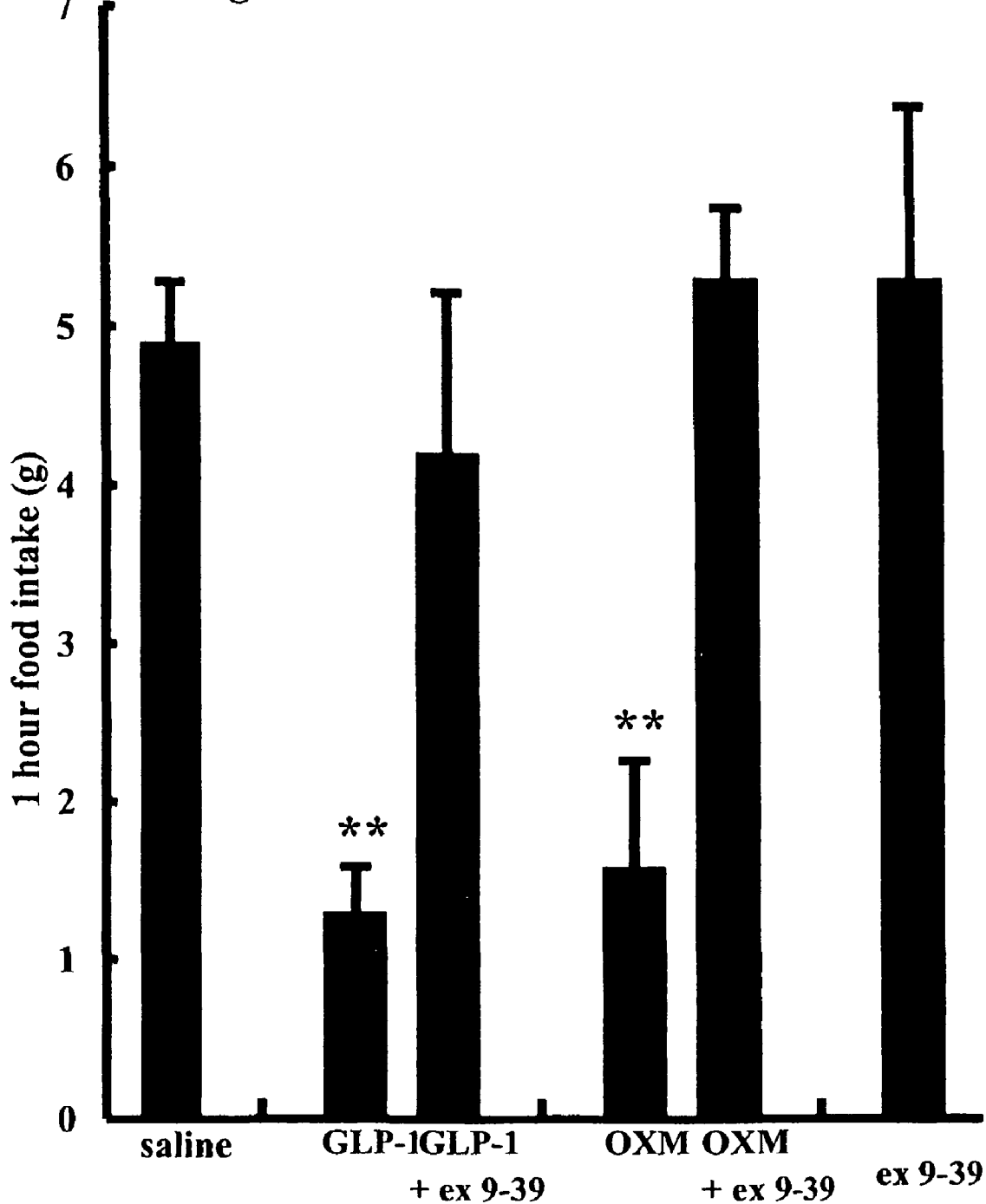

A

B

A)

B)

C)

SEQUENCE LISTING

```
<160> NUMBER OF SEQ ID NOS: 5

<210> SEQ ID NO 1
<211> LENGTH: 37
<212> TYPE: PRT
<213> ORGANISM: Bos sp

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Lys Asn Asn Ile Ala
        35

<210> SEQ ID NO 2
<211> LENGTH: 36
<212> TYPE: PRT
<213> ORGANISM: Lophius sp.

<400> SEQUENCE: 2

His Ser Glu Gly Thr Phe Ser Asn Asp Tyr Ser Lys Tyr Leu Glu Asp
1               5                   10                  15

Arg Lys Ala Gln Glu Phe Val Arg Trp Leu Met Asn Asn Lys Arg Ser
            20                  25                  30

Gly Val Ala Glu
        35

<210> SEQ ID NO 3
<211> LENGTH: 36
<212> TYPE: PRT
<213> ORGANISM: Anguilla sp.

<400> SEQUENCE: 3

His Ser Gln Gly Thr Phe Thr Asn Asp Tyr Ser Lys Tyr Leu Glu Thr
1               5                   10                  15

Arg Arg Ala Gln Asp Phe Val Gln Trp Leu Met Asn Ser Lys Arg Ser
            20                  25                  30

Gly Gly Pro Thr
        35

<210> SEQ ID NO 4
<211> LENGTH: 37
<212> TYPE: PRT
<213> ORGANISM: Homo sapiens

<400> SEQUENCE: 4

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30
```

```
Arg Asn Asn Ile Ala
        35

<210> SEQ ID NO 5
<211> LENGTH: 30
<212> TYPE: PRT
<213> ORGANISM: Homo sapiens

<400> SEQUENCE: 5

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

OXYNTOMODULIN FOR PREVENTING OR TREATING EXCESS WEIGHT

The present application is a nationalization of PCT Application Ser. No. PCT/GB02/04082, filed Sep. 9, 2002, which claims priority to British priority application Ser. No. 0121709.0, filed Sep. 7, 2001.

The present invention relates to compositions and methods for use in weight loss in mammalian animals.

One of the diseases with the highest incidence but which lacks effective treatment is obesity. It is a debilitating condition which reduces quality of life and substantially increases the risk of other diseases.

In the USA 25% of the adult population is now considered to be clinically obese. It has been estimated that $45 billion of US healthcare costs, or 8% per annum of total healthcare spending, is a direct result of obesity. In Europe the problem is increasing. It has been predicted that without new approaches over 20% of the UK population will be clinically obese by 2005. The fact that obesity is a metabolic disease is being increasingly recognized by the medical profession and the health authorities. There is, however, a shortage of effective and safe drugs which can be used in conjunction with diet and exercise for the long-term management of obesity.

It is an object of the present invention to provide such drugs and also to provide means to identify and further develop such drugs.

Preproglucagon is a 160 amino acid polypeptide which is cleaved in a tissue specific manner by prohormone convertase-1 and -2 giving rise to a number of products with a variety of functions in both the central nervous system (CNS) and peripheral tissues. In the intestine and in the CNS, the major post-translational products of preproglucagon cleavage are glucagon-like peptide-1 (GLP-1), glucagon-like peptide-2 (GLP-2), glicentin and oxyntomodulin (OXM), as shown in Figure A. To date, no role in the CNS has been demonstrated for OXM.

While GLP-1 and GLP-2 have been shown to inhibit food intake, no such role has been demonstrated for the distinct peptide OXM. The importance of OXM as a biologically active peptide has not been demonstrated.

It has been surprisingly found that contrary to expectations, the OXM peptide can inhibit food intake and reduce weight.

Accordingly, the present invention provides, according to a first aspect, a composition comprising OXM, for use in the prevention or treatment of excess weight in a mammal.

In this text, the term "oxyntomodulin" is the same as "OXM" and relates to any composition which includes an OXM peptide sequence or an analogue thereof as follows:

OXM sequences are well known and documented in the art. The present invention relates to all of the sequences recited herein including, in particular, the OXM human sequence (which is the same as the rat, and hamster OXM sequence), as follows:

```
                                          (SEQ ID NO:4)
His Ser Gln Gly Thr Phe Thr Ser Asp Tyr

Ser Lys Tyr Leu Asp Ser Arg Arg Ala Gln

Asp Phe Val Gln Trp Leu Met Asn Thr Lys

Arg Asn Arg Asn Asn Ile Ala.
```

The OXM angler fish sequence as follows:

```
                                          (SEQ ID NO:2)
His Ser Glu Gly Thr Phe Ser Asn Asp Tyr

Ser Lys Tyr Leu Glu Asp Arg Lys Ala Gln

Glu Phe Val Arg Trp Leu Met Asn Asn Lys

Arg Ser Gly Val Ala Glu.
```

And the eel OXM sequence as follows:

```
                                          (SEQ ID NO:3)
His Ser Glu Gly Thr Phe Thr Asn Asp Tyr

Ser Lys Tyr Leu Glu Thr Arg Arg Ala Gln

Asp Phe Val Gln Trp Leu Met Asn Ser Lys

Arg Ser Gly Gly Pro Thr.
```

The term OXM used in this text also covers any analogue of the above OXM sequence, wherein the histidine residue at position 1 is maintained or replaced by an aromatic moiety carrying a positive charge or a derivative thereof, preferably wherein the moiety is an amino acid, more preferably wherein it is a histidinederivative, while 1, 2, 3, 4, 5, 6, 7, 8, 9, 10, 11, 12, 13, 14, 15, 16, 17, 18, 19, 20, 21 or 22 of the other amino acids in the above OXM sequence can be independently replaced by any other independently chosen amino acid, with the exception of histidine in position 1.

Any one or more (to 22) other alpha-amino acid residue in the sequence can be independently replaced by any other one alpha-amino acid residue. Preferably, any amino acid residue other than histidine is replaced with a conservative replacement as well known in the art i.e. replacing an amino acid with one of a similar chemical type such as replacing one hydrophobic amino acid with another.

As discussed above, 1 to 22 of the amino acids can be replaced. In addition to the replacement option above, this may be by a non-essential or modified or isomeric form of an amino acid. For example, 1 to 22 amino acids can be replaced by an isomeric form (for example a D-amino acid), or a modified amino acid, for example a nor-amino acid (such as norleucine or norvaline) or a non-essential amino acid (such as taurine). Furthermore, 1 to 22 amino acids may be replaced by a corresponding or different amino acid linked via its side chain (for example gamma-linked glutamic acid). For each of the replacements discussed above, the histidine residue at position 1 is unaltered or defined above.

In addition, 1, 2, 3, 4 or 5 of the amino acid residues can be removed from the OXM sequence with the exception of histidine at the 1 position (or as defined above). The deleted residues may be any 2, 3, 4 or 5 contiguous residues or entirely separate residues.

The C-terminus of the OXM sequence may be modified to add further amino acid residues or other moieties. The OXM above may be provided as the corresponding salt thereof. Examples of pharmaceutically acceptable salts of OXM and its analogues include those derived from organic acids such as methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methyl amine, dimethylamine, and trimethylamine, guanidine; N-methylglucosamine; N-methylpiperazine; morpholine; ethylenediamine; N-benzylphenethylamine; tris(hydroxymethyl) aminomethane; and the like.

Salts may be prepared in a conventional manner using methods well known in the art. Acid addition salts of said basic compounds may be prepared by dissolving the free base compounds in aqueous or aqueous alcohol solution or other suitable solvents containing the required acid. Where OXM contains an acidic function a base salt of said compound may be prepared by reacting said compound with a suitable base. The acid or base salt may separate directly or can be obtained by concentrating the solution eg. by evaporation. OXM may also exist in solvated or hydrated forms.

The OXM of the present invention may be conjugated to one or more groups such as a lipid, sugar, protein or polypeptide. The OXM can be conjugated by being attached to the group (for example via a covalent or ionic bond) or can be associated therewith. The conjugated link is preferably not through the C or N terminus amino acid, when the OXM is attached to the group. The OXM can be conjugated to a polymer such as polyethylene glycol, polyvinylpyrrolidone, polyvinylalcohol, polyoxyethylene-polyoxypropylene copolymers, polysaccharides such as cellulose, cellulose derivatives, chitosan, acacia gum, karaya gum, guar gum, xanthan gum, tragacanth, alginic acid, carrageenan, agarose, and furcellarans, dextran, starch, starch derivatives, hyaluronic acid, polyesters, polyamides, polyanhydrides, and poly-ortho esters.

The OXM can be chemically modified. In particular, the amino acid side chains, the N terminus and/or the C acid terminus of OXM can be modified. For example, the OXM can undergo one or more of alkylation, disulphide formation, metal complexation, acylation, esterification, amidation, nitration, treatment with acid, treatment with base, oxidation or reduction. Methods for carrying out these processes are well known in the art. In particular the OXM is provided as a lower alkyl ester, a lower alkyl amide, a lower dialkyl amide, an acid addition salt, a carboxylate salt or an alkali addition salt thereof. In particular, the amino or carboxylic termini of the OXM may be derivatised by for example, esterification, amidation, acylation, oxidation or reduction. In particular, the carboxylic terminus of the OXM can be derivatised to form an amide moiety.

The OXM can be treated with metals, in particular with divalent metals. For the purposes of this invention the OXM can therefore be provided in the presence of one or more of the following metals, zinc, calcium, magnesium, copper, manganese, cobalt, molybdenum or iron.

The OXM can be provided in combination with a pharmaceutically acceptable carrier or diluent. Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration). The OXM can be provided as a crystalline solid, a powder, an aqueous solution, a suspension or in oil.

The compositions according to the invention for use in the aforementioned indications may be administered by any convenient method, for example by oral (including by inhalation), parenteral, mucosal (e.g. buccal, sublingual, nasal), rectal, subcutaneous or transdermal administration and the compositions adapted accordingly.

For oral administration, the composition can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

The OXM can be used as a prophylaxis to prevent excess weight gain or can be used as a therapeutic to lose excess weight.

The excess weight is typically obesity, although the mammal will not be certified as clinically obese in order to be suffering from excess weight. The OXM may be in liquid, solid or semi-solid form.

In today's society, the prevention or treatment of excess weight in a mammal is a real need. Preferably the mammal is a human, although it may also include other mammalian animals, such as horses, canine animals (in particular domestic canine animals), feline animals (in particular domestic feline animals) as well as mammals which are produced for meat, such as porcine, bovine and ovine animals. The present invention can be used to prevent excess weight in such animals in order to maximise lean meat production.

Throughout this text, the term "prevention" means any effect which mitigates any excess weight, to any extent. Throughout this text, the term "treatment" means amelioration of excess weight, to any extent.

According to a second aspect, the present invention provides a method for the prevention or treatment of excess weight in a mammal, the method comprising administering a composition comprising OXM to a mammal. The mammal is likely to be in need of prevention or treatment of excess weight. The weight loss may be cosmetic. The composition comprising OXM will be administered in an effective concentration.

All preferred features of the first aspect of the invention, also apply to the second.

A third aspect of the present invention provides a method for cosmetic weight loss in a mammal, the method comprising administering a composition comprising OXM to a mammal. In this circumstance, the weight loss is purely for the purposes of cosmetic appearance.

All preferred features of the first and second aspects also apply to the third.

Without being bound to this theory, it is understood that the present invention provides the prevention or treatment of excess weight by the administration of OXM which acts as an inhibitor to food intake to the mammalian body. Such reduced food intake results in the prevention or treatment of excess weight in a mammal. In this text the term "food" includes a substance which is ingested and which has calorific value.

A fourth aspect to the present invention provides the use of OXM in the manufacture of a medicament for the prevention or treatment of excess weight.

All preferred features of the first and third aspects, all apply to the fourth.

The first, second and fourth aspects of the invention relate to medicaments, the particular dosage regime for which will ultimately be determined by the attending physician and will take into consideration such factors as the OXM being used, animal type, age, weight, severity of symptoms and/or severity of treatment to be applied, method of administration of the medicament, adverse reaction and/or contra indications. Specific defined dosage ranges can be determined by standard designed clinical trials with patient progress and recovery being fully monitored.

Such trials may use an escalating dose design using a low percentage of the maximum tolerated dose in animals as the starting dose in man.

The fifth aspect of the present invention relates to the use of OXM to identify an agent which inhibits food intake in a mammal. This aspect of the invention provides a means to identify and develop further suitable medicaments for the prevention or treatment of excess weight.

The use of OXM may include the use of the peptide itself or may include the use of the theoretical or models characteristics of OXM. The functional or structural characteristics of OXM utilised may be of a peptide itself or may be of a computer-generated model, a physical two or three-dimensional model or an electrical generated (e.g. computer generated) primary, secondary or tertiary structure, as well as the pharmacophore (three-dimensional electron density map) or its X-ray crystal structure.

The structural characteristics may enable the identification of potential agents that may interact with OXM thereby affecting it's function. The identification may be by computer modelling and/or rational drug design.

Preferred features of each aspect of the invention are as for each of the other aspects mutatis mutandis.

The present invention is now described by way of example only and with reference to the following figures, in which:

Figure A is a graphical representation of preproglucagon and its component parts;

FIG. 1 is a comparison of the effects of ICV and iPVN proglucagon-derived and related products on food intake in fasted rats. FIG. 1A illustrates the cumulative food intake (g) up to 8 h after ICV injection of GLP-1, OXM, glucagon, or glicentin (all 3 nmol) into fasted animals. *, $P<0.05$ vs. saline control. FIG. 1B illustrates cumulative food intake (g) up to 24 h after an acute iPVN injection of GLP-1, OXM (both 1 nmol), or exendin-4 (0.03 nmol) into fasted animals. *, $P<0.01$ vs. saline control for all groups at 1, 2, and 4 h. *, $P<0.05$ vs. saline control for exendin-4 only at 8 h;

FIG. 2 shows two graphs of the effects of ICV and iPVN OXM on food intake in fasted rats. FIG. 2A, cumulative food intake (g) up to 8 h after an acute ICV injection of OXM (0.3, 1, 3, or 10 nmol). FIG. 2B, cumulative food intake (g) up to 8 h after an acute iPVN injection of OXM (0.1, 0.3, or 1.0 nmol) into fasted animals. *, $P<0.05$ vs. saline control;

FIG. 3 shows two bar graphs of the effect of ICV OXM at the onset of the dark phase. Sated rats received an ICV injection of OXM, GLP-1 (3 nmol), or saline at the onset of the dark phase. Food intake (grams; A) and behaviors (B) at 1 h postinjection were determined. *, $P<0/05$ vs. saline control;

FIG. 4 shows two bar graphs of the inhibition of OXM and GLP-1 effects on food intake by exendin-(9-39). FIG. 4A, food intake 1 h after an acute ICV injection of GLP-1 (3 nmol), GLP-1 plus exendin-(9-39) (30 nmol), OXM (3 nmol), OXM and exendin-(9-39) (30 nmol), or exendin-(9-39) alone (30 nmol). FIG. 4B, food intake after an acute iPVN injection of GLP-1 (1 nmol), GLP-1 and exendin-(9-39) (10 nmol), OXM (1 nmol), OXM and exendin-(9-39) (10 nmol), or exendin-(9-39) alone (10 nmol) into fasted animals. **, $P<0.005$ vs. saline control;

FIG. 5 is a graph of the competition of [$^{125}$I] GLP-1 binding in rat hypothalamic membranes by GLP-1 and OXM;

FIG. 6 illustrates the effect of a) IP OXM (30, 100 and 300 nmol/kg in 500 μl saline) or saline on cumulative food intake (g) in 24-hour fasted rats injected during the early dark phase (closed squares=saline, open circles=OXM 30 nmol/kg, closed triangles=OXM 100 nmol/kg, open triangles=OXM 300 nmol/kg); and b) IP OXM (30 and 100 nmol/kg in 500 μl saline) or saline on cumulative food intake in non-fasted rats injected prior to the onset of the dark phase (closed squares=saline, open circles=OXM 30 nmol/kg, closed triangles=OXM 100 nmol/kg). *$P<0.05$ vs. saline;

Figure 10:
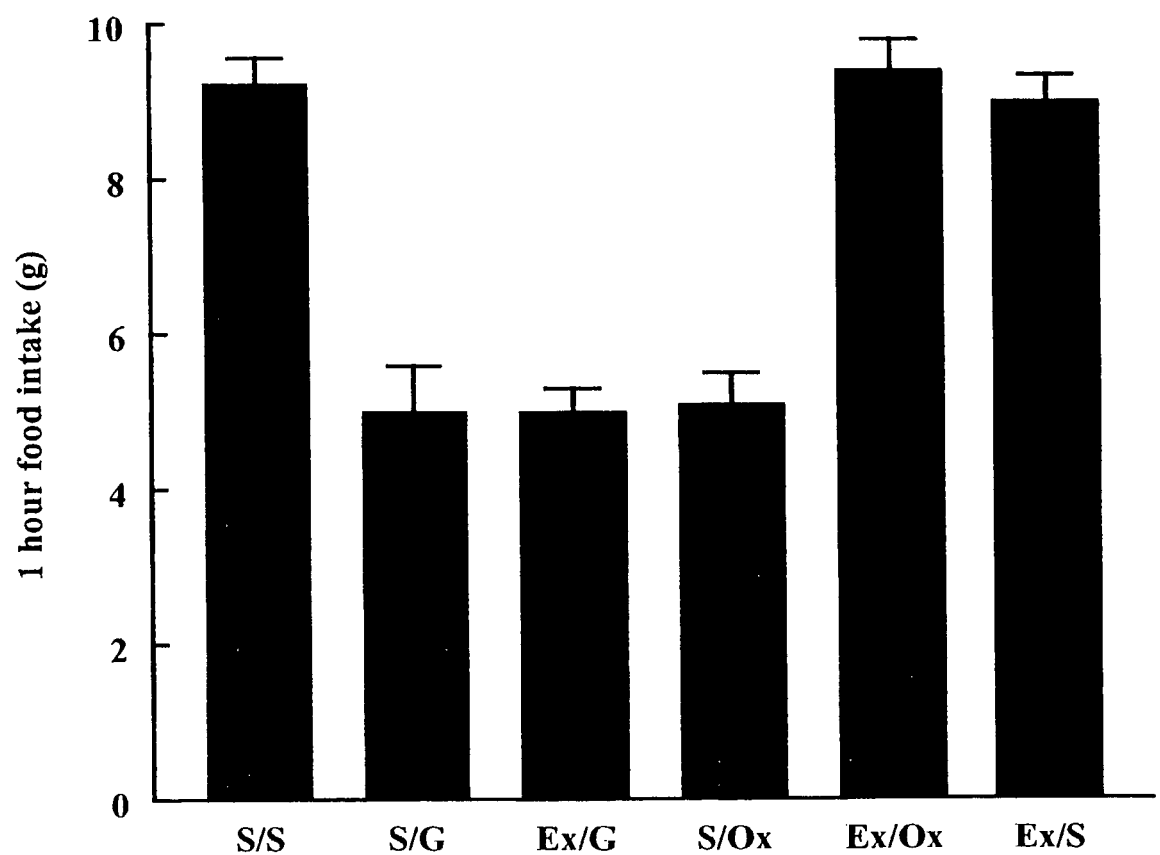
Figure 11A:
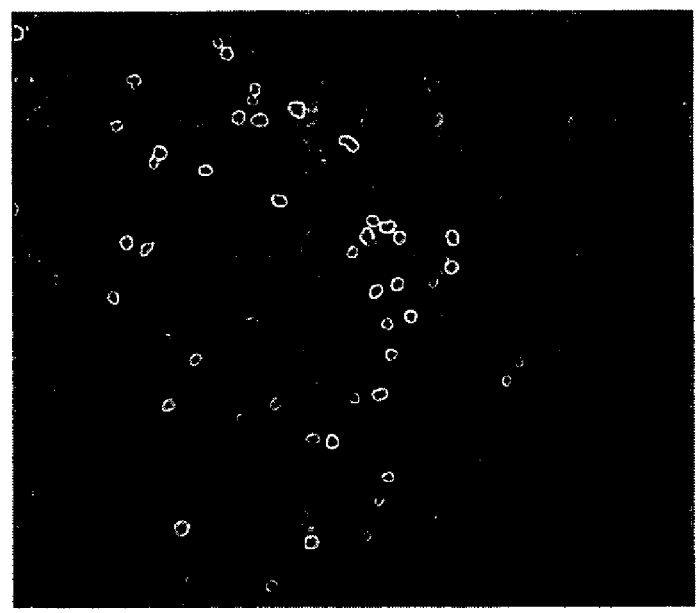
Figure 11A:
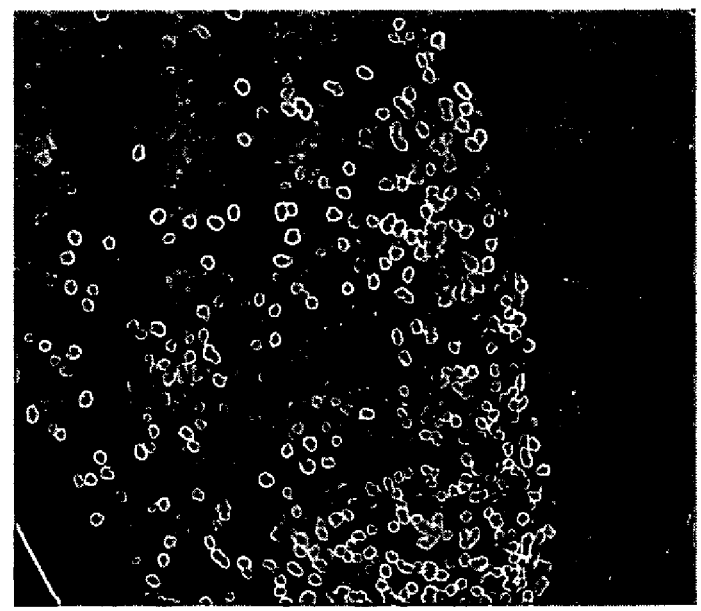
Figure 11B:
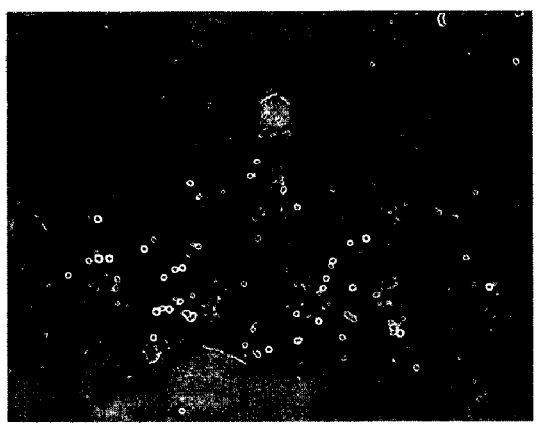
Figure 11B:
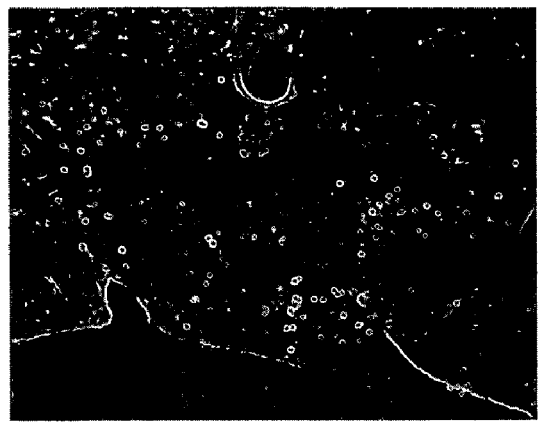
Figure 11B:
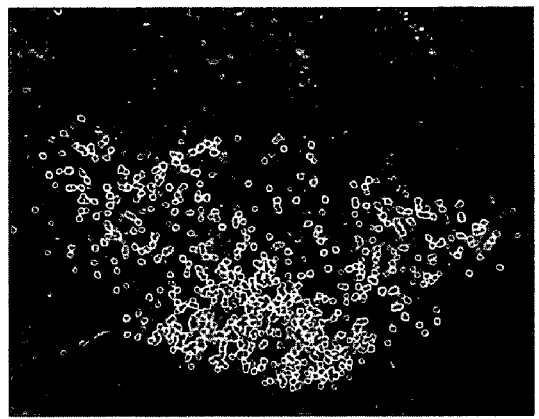

FIG. 10 illustrates the effect of iARC administration of exendin 9-39 (5 nmoles) or saline injected 15 minutes prior to IP administration of OXM (30 nmol/kg), GLP-1 (30 nmol/kg) or saline on 1 hour food intake (g). (S=saline, G=GLP-1 (30 nmol/kg), Ox=OXM (30 nmol/kg), Ex=exendin 9-39 (5 nmoles));

FIG. 11a illustrates the expression of fos-like immunoreactivity in response to A) IP saline or B) IP OXM (50 nmol/kg) in the arcuate nucleus of the hypothalamus (×40 magnification). ***P<0.005 vs. saline; and FIG. 11b illustrates the expression of fos-like immunoreactivity in response to A) IP saline, B) IP OXM (50 nmol/kg) or C) IP CCK (15 nmol/kg) in the NTS and AP of the brainstem.

EXAMPLES

A—OXM Causes a Potent Decrease in Fasting-induced Refeeding When Injected Both ICV and iPVN Peptides and Chemicals GLP-1, glicentin, glucagon, and SP-1 were purchased from Peninsula Laboratories, Inc. (St. Helens, UK). OXM was purchased from IAF BioChem Pharma (Laval, Canada). Exendin-4 and exendin-(9-39) were synthesised at Medical Research Council, Hemostasis Unit, Clinical Sciences Center, Hammersmith Hospital, London, UK using F-moc chemistry on an 396 MPS peptide synthesiser (Advanced ChemTech, Inc.) and purified by reverse phase HPLC on a $C_8$ column (Phenomex, Macclesfield, UK). The correct molecular weight was confirmed by mass spectrometry. All chemicals were purchases from Merck & Co. (Lutterworth, Leicester, UK) unless otherwise stated.

Animals

Adult male Wistar rats (ICSM, Hammersmith Hospital) were maintained in individual cages under controlled conditions of temperature (21-23° C.) and light (12 h of light, 12 h of darkness) with ad libitum access to food (RM1 diet, Special Diet Services UK Ltd., Witham, UK) and tap water. Animals were handled daily after recovery from surgery until completion of the studies. All animal procedures undertaken were approved by the British Home Office Animals (Scientific Procedures Act 1986 (Project License PIL 90/1077).

ICV and iPVN Cannulation and Infusions of Test Compounds

Animals had permanent stainless steel guide cannulas (Plastics One, Roanoke, Va.) stereotactically implanted ICV or iPVN. All studies were carried out in the early light phase, between 0900-1100 h, after a 24-h fast, and food intake was measured 1, 2, 4, 8, and 24 h postinjection.

Feeding Study Protocols

Comparison of the effect of proglucagon-derived products and related peptides on food intake.

In study 1a, rats were injected ICV with 10 µl saline, GLP-1 (13 nmol), OXM (3 nmol), glucagon (3 nmol), or glicentin (3 nmol; n=8/group).

In all studies, OXM with the following sequence was used:

```
                                              (SEQ ID NO:1)
    His Ser Gln Gly Thr Phe Thr Ser Asp Tyr

Ser Lys Tyr Leu Asp Ser Arg Arg Ala Gln

Asp Phe Val Gln Trp Leu Met Asn Thr Lys

Arg Asn Lys Asn Asn Ile Ala.
```

Human GLP-1 with the following sequence was used:

```
                                                SEQ ID NO:5
    His Ala Glu Gly Thr Phe Thr Ser Asp Val

Ser Ser Tyr Leu Glu Gly Gln Ala Ala Lys

Glu Phe Ile Ala Trp Leu Val Lys Gly Arg.
```

In study 1b, rats were injected iPVN with 1µ saline, GLP-1 (1.0 nmol), OXM (1.0 nmol), glicentin (1.0 nmol), glucagon (1.0 nmol), or SP-1 (3.0 nmol; n=12-15/group). Exendin-4, when injected ICV, inhibits food intake more potently than GLP-1. Therefore, exendin-4 was injected iPVN at a dose of 0.03 nmol.

Investigation of the Effect of Increasing Doses of OXM on Food Intake

In study 2a, rats were injected ICV with saline, GLP-1 (3 nmol), or OXM (0.3, 1, 3 or 10 nmol; n=8/group). In study 2b, rats were injected iPVN with saline, GLP-1 (1.0 nmol), or OXM (0.1, 0.3, or 1.0 nmol; n—12-15/group). To assess whether OXM acts via the GLP-1 receptor, a study using the GLP-1 receptor antagonist exendin-(9-39) was performed.

Night Time Feeding and Behavioural Analysis.

Study 3. It is possible that OXM inhibits food intake via nonspecific taste aversion, and that it is not a true satiety factor. Therefore, ICV cannulated rats were administered GLP-1 (3 nmol), OXM (3 nmol), or saline (n=6/group) at the onset of the dark phase. Food intake was measured 1 h postinjection (study 3a), and behaviour was assessed (study 3b). Rats were observed for 1 h postinjection using a behavioural score sheet.

In study 4a, rats were injected with ICV with saline, GLP-1 (3 nmol), GLP-1 (3 nmol) plus exendin-(9-39) (30 nmol), OXM (3 nmol), OXM (3 nmol) plus exendin-(9-39) (30 nmol), or exendin-(9-39) alone (30 nmol). In study 4b, rats were iPVN injected with saline, GLP-1 (1 nmol), GLP-1 (1 nmol) plus exendin-(9-39) (10 nmol), OXM (1 nmol), OXM (1 nmol) plus exendin-(9-39) (10 nmol), or exendin-(9-39) alone (10 nmol; n=10-12/group).

Receptor Binding Assays. Study 5.

Receptor binding assays were performed in a final volume of 0.5 ml rat hypothalamic membranes (200 µg protein), 500 Bq (100 pM) [$^{125}$I]GLP-1, and unlabeled competing peptides (GLP-1 and OXM) as specified. Membranes were incubated at room temperature for 90 min. Bound and free radioactivity were separated by centrifugation (2 min, 4° C.). Pelleted membranes were washed with assay buffer (0.5 ml, ice-cold), and the membranes were centrifuged as described above. The supernatant was removed, and the radioactivity in the pellet was counted using a γ-counter. Specific (saturable) binding was calculated as the difference between the amount of [$^{125}$I] GLP-1 bound in the absence (total binding) and presence of 1 μm GLP-1 or OXM (nonsaturable binding). All curves were constructed with points in triplicate. $IC_{50}$ values were calculated using the Prism 3 program (GraphPad Software, Inc., San Diego, Calif.).

Statistics

For food intake analyses, data are presented as the mean±SEM. Statistical differences between experimental groups were determined by ANOVA, followed by a post-hoc least significant difference test (Systat 8.0, Evanston, Ill.). For behavioural analyses, data are expressed as the median number of occurrences of each behaviour and the range. Comparisons between groups were made using the Mann-Whitney U test (Systat 8.0). In all cases, $P<0.05$ was considered statistically significant.

Results

Comparison of the effects of proglucagon-derived products and related peptides on food intake ICV Administration.

Figure 1A:
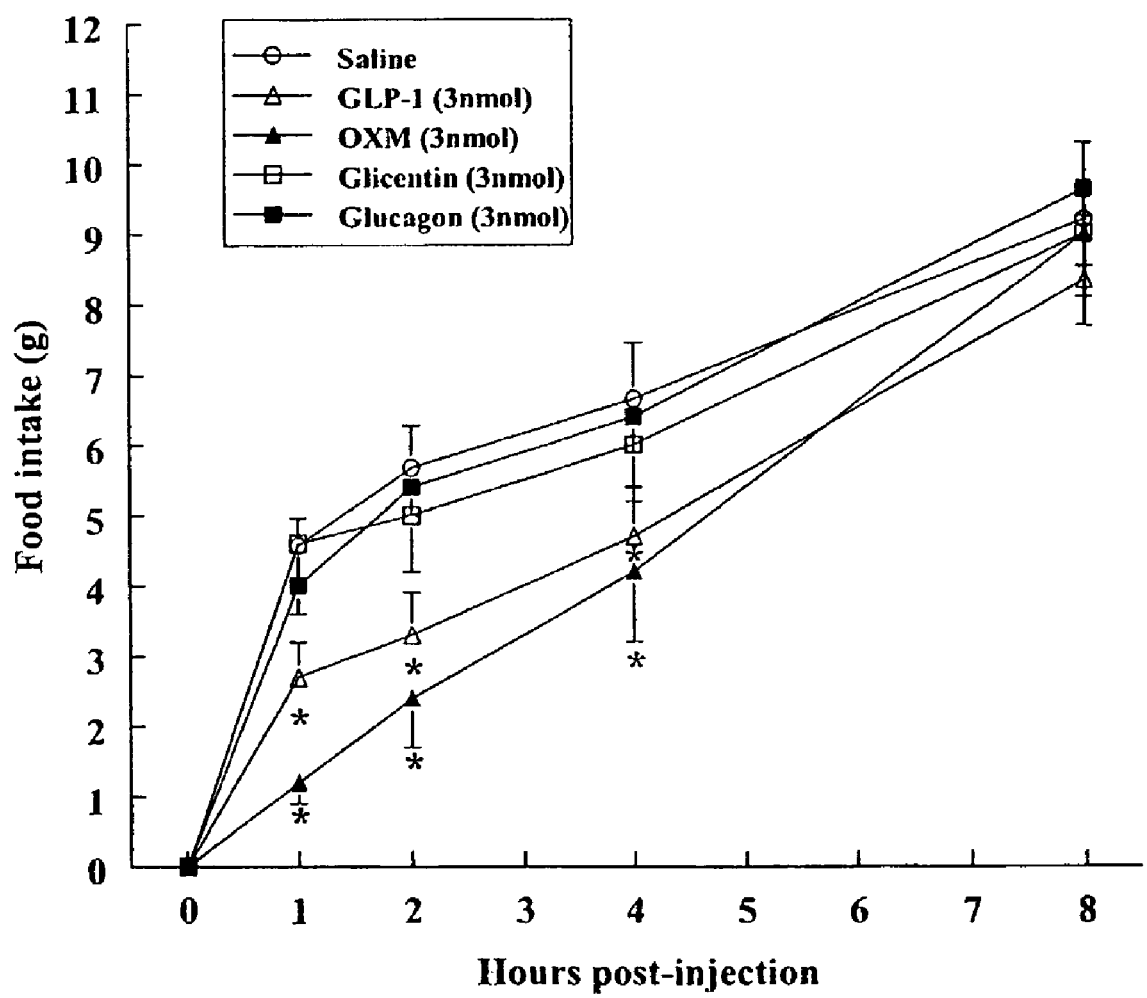

In study 1a, OXM and GLP-1 (3 nmol) significantly reduced refeeding. This inhibition of food intake lasted until 4 h postinjection (FIG. 1A). Glucagon and glicentin (3 nmol) failed to affect food intake at any time point (FIG. 1A).

iPVN Administration.

Figure 1B:
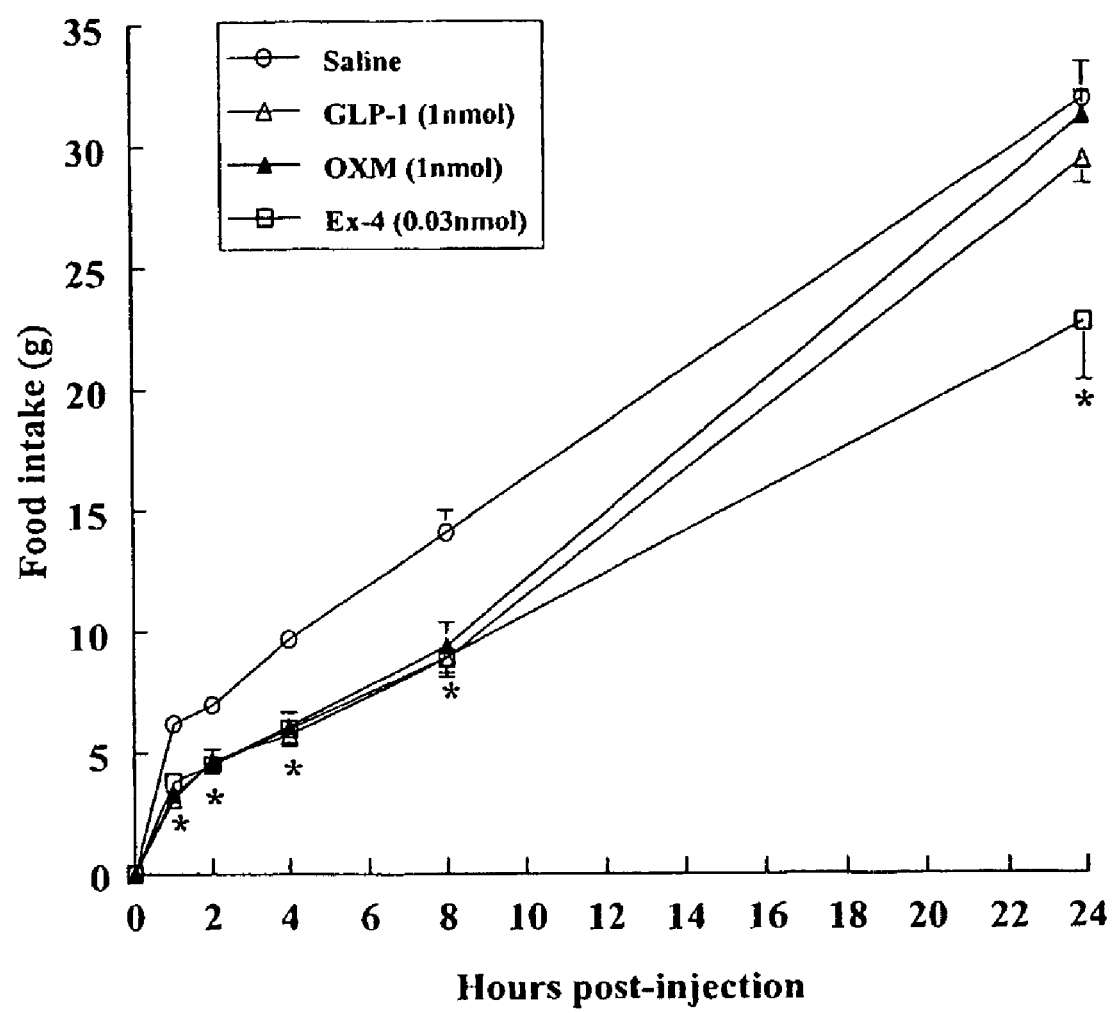

In study 1b, OXM, GLP-1 (3 nmol) and exendin-4 (0.03 nmol) also inhibited refeeding when injected iPVN. This inhibition lasted at least 8 h postinjection, longer than when injected ICV (FIG. 1B). Glicentin, glucagon (1 nmol), and SP-1 (3 nmol) failed to affect food intake at any time point when injected iPVN.

Effects of Increasing Doses of OXM on Food Intake

ICV Administration.

Figure 2A:
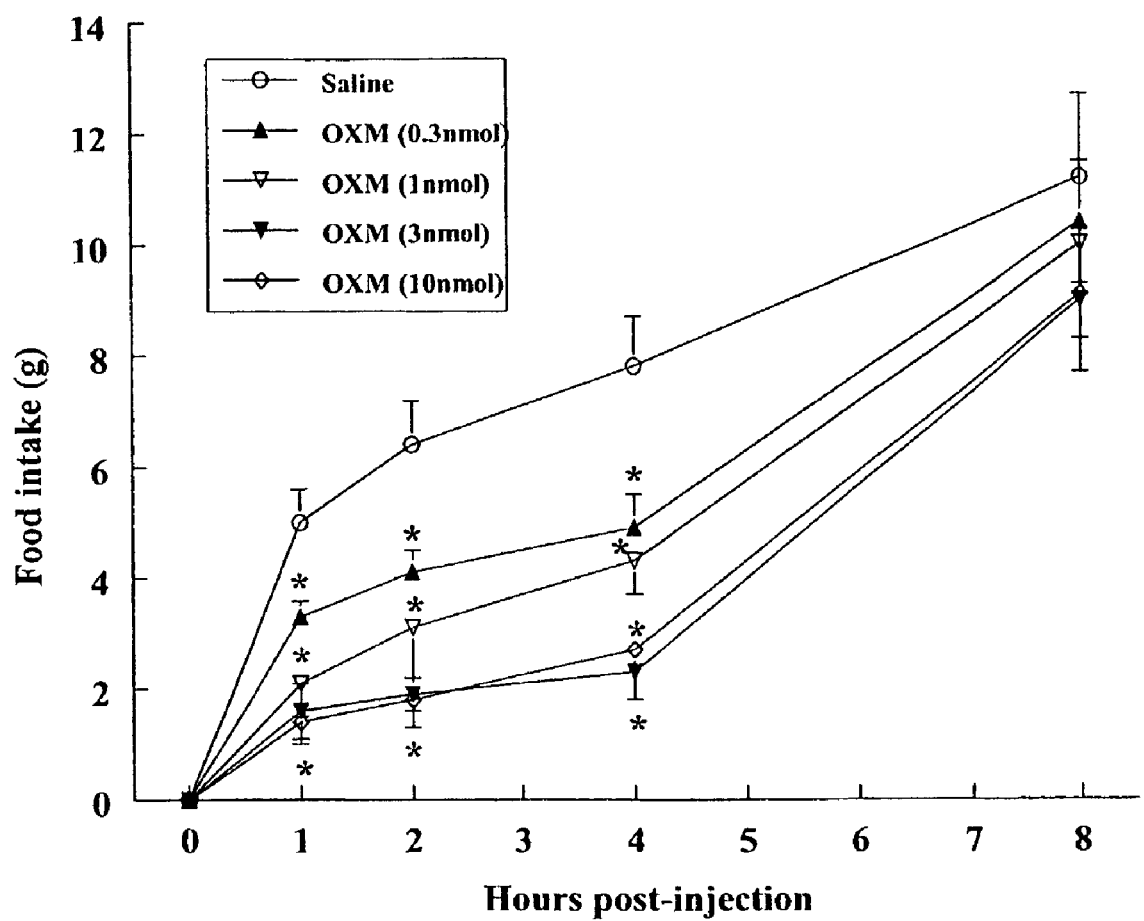

In study 2a, when injected ICV, OXM reduced refeeding in a dose-dependent manner, reaching a maximal effect at a dose of 3 nmol 1, 2, and 4 h postinjection (FIG. 2A).

iPVN Administration.

Figure 2B:
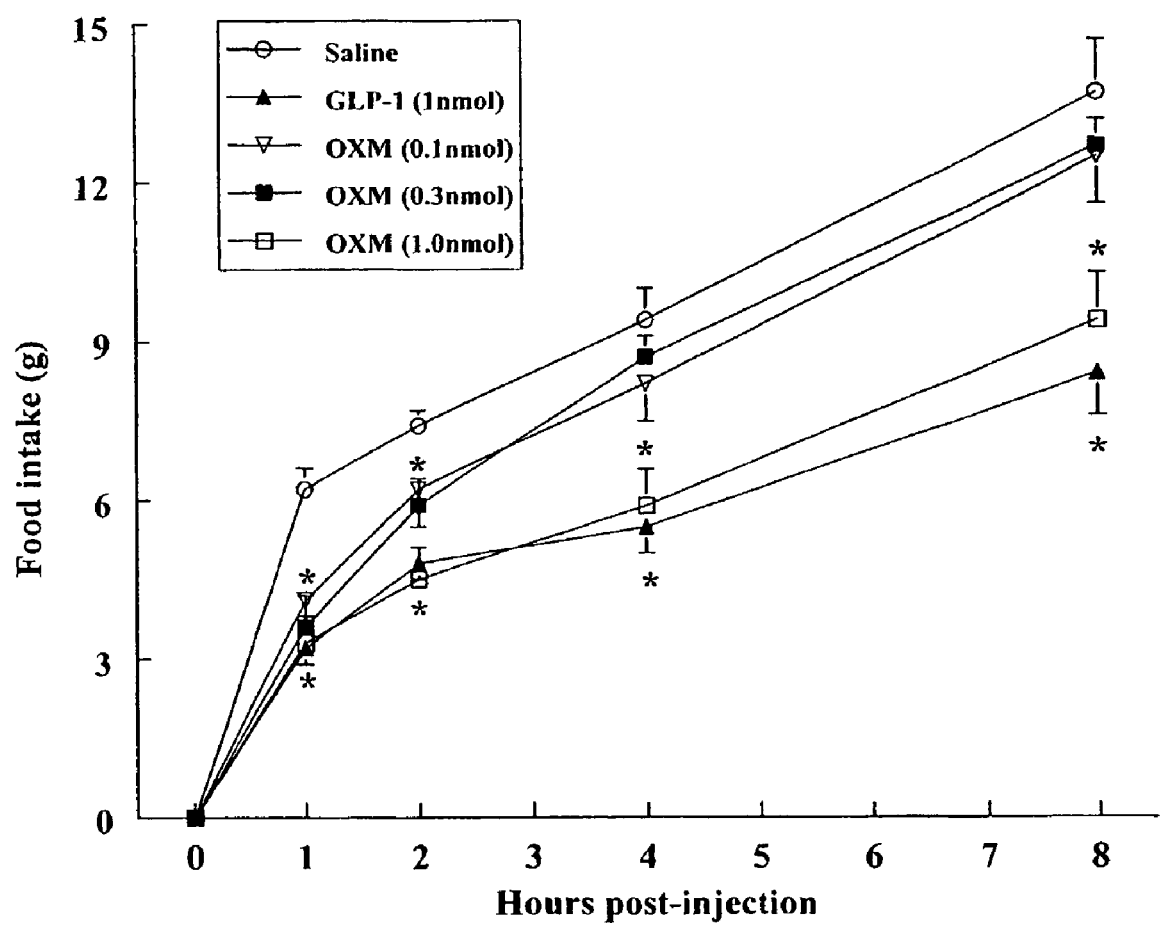

In study 2b, food intake was significantly reduced by iPVN-injected GLP-1 and OXM (both 1 nmol) until 8 h postinjection (FIG. 2B).

Effect of OXM in ICV-cannulated Sated Rats at the Onset of the Dark Phase.

The dark phase is the rats' natural feeding time. Therefore, assessing the effect of a putative satiety factor in non-fasted animals at this time would represent a more physiological effect.

Effect of OXM on Food Intake.

Figure 3A:
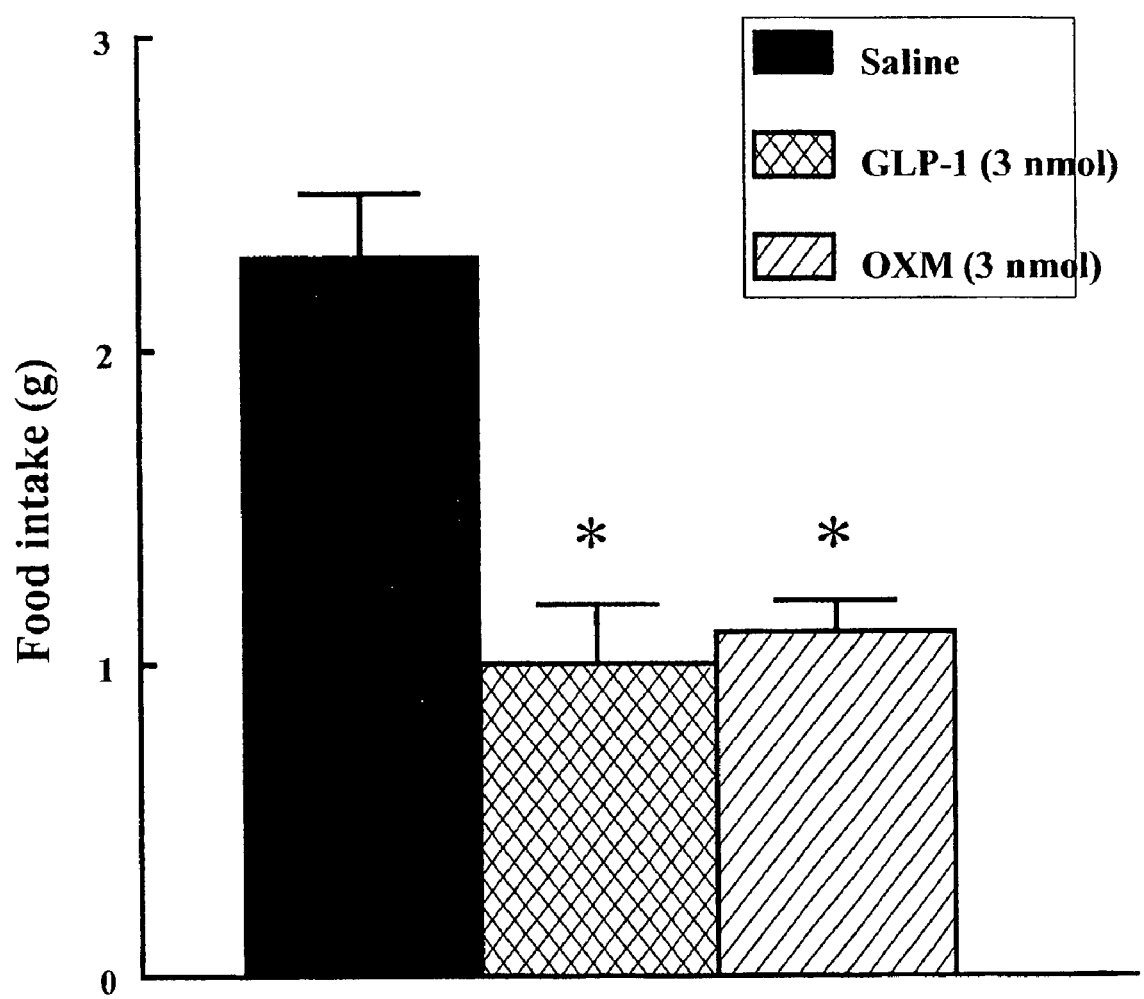

In study 3a, when injected in the early dark phase, both GLP-1 and OXM (3 nmol) significantly reduced food intake compared with that of saline-treated animals 1 h postinjection [FIG. 3A].

Observation of Behaviour After ICV Injection of OXM.

Figure 3B:
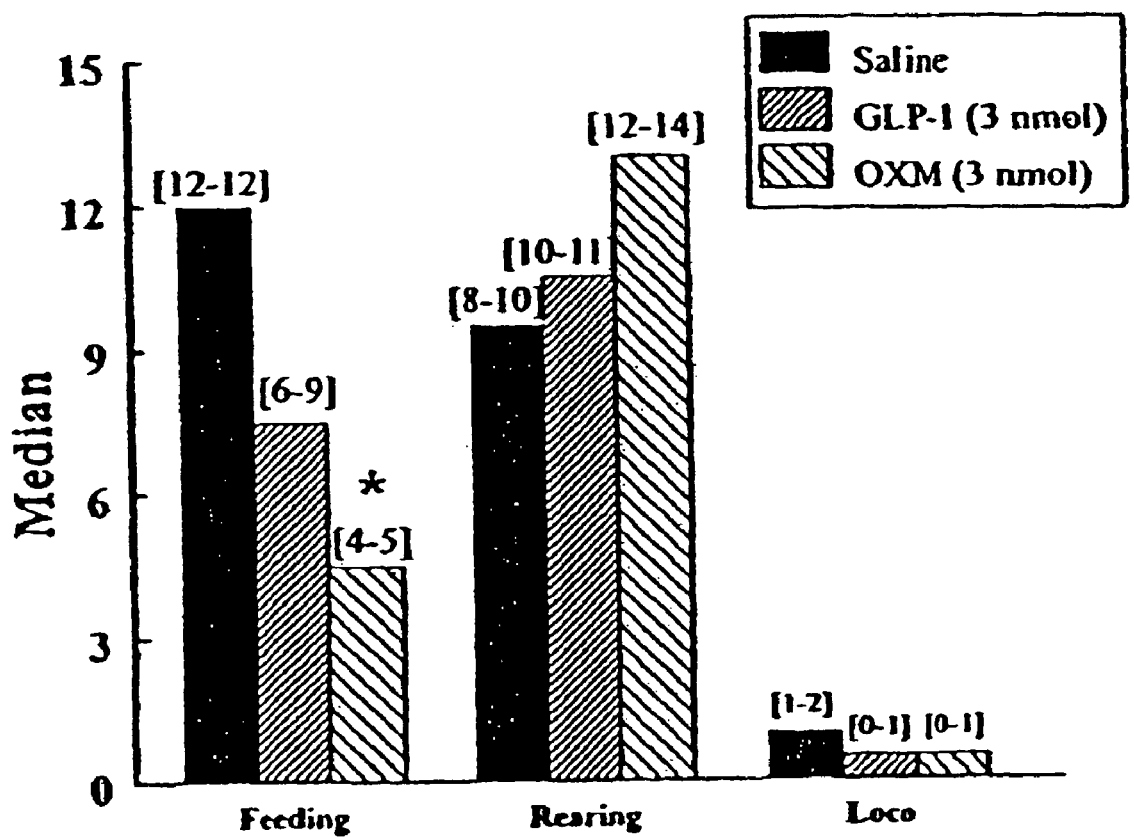

ICV administration of OXM (3 nmol) in the early dark phase led to a significant decrease in feeding episodes (study 3a) and an increase in rearing behaviour (study 3b) [FIG. 3B]. There was no change in grooming, still, head down, burrowing, or locomotion episodes.

To assess whether OXM acts via the GLP-1R, a study using the GLP-1R antagonist, exendin-(9-39) was performed.

ICV Administration. Study 4.

ICV coadministration of the GLP-1 receptor antagonist exendin-(9-39) with GLP-1 at a ratio of 10:1 (antagonist/agonist) blocked the anorectic effects of GLP-1 [FIG. 4A]. Furthermore, coadministration of exendin-(9-39) with OXM resulted in attenuation of the anorectic effect of OXM [FIG. 4A].

iPVN Administration.

Figure 4B:
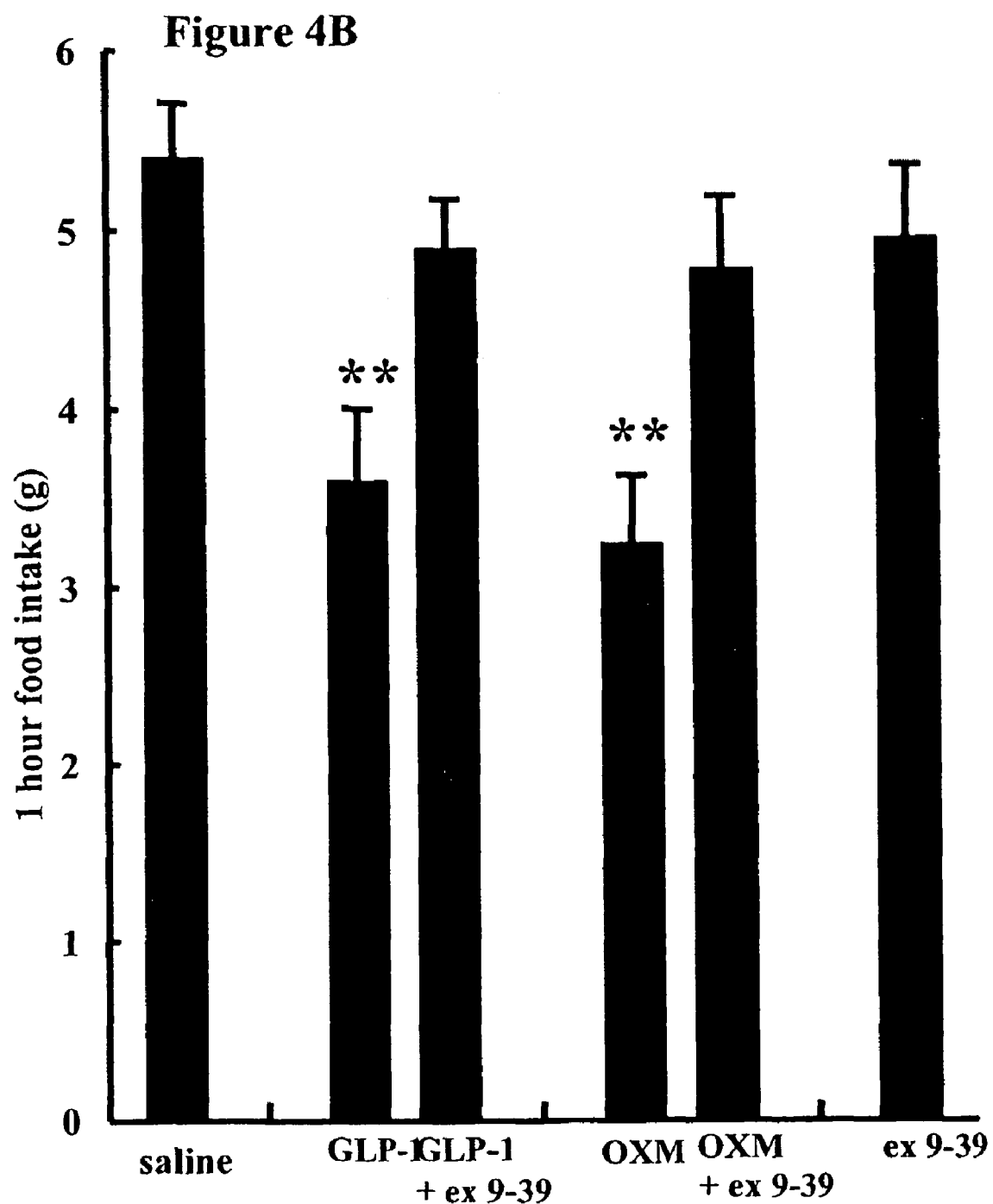

Similarly, when injected iPVN, the anorectic effects of both GLP-1 and OXM were blocked when coinjected with exendin-(9-39) [FIG. 4B].

Receptor Binding Assays. Study 5.

Figure 5:
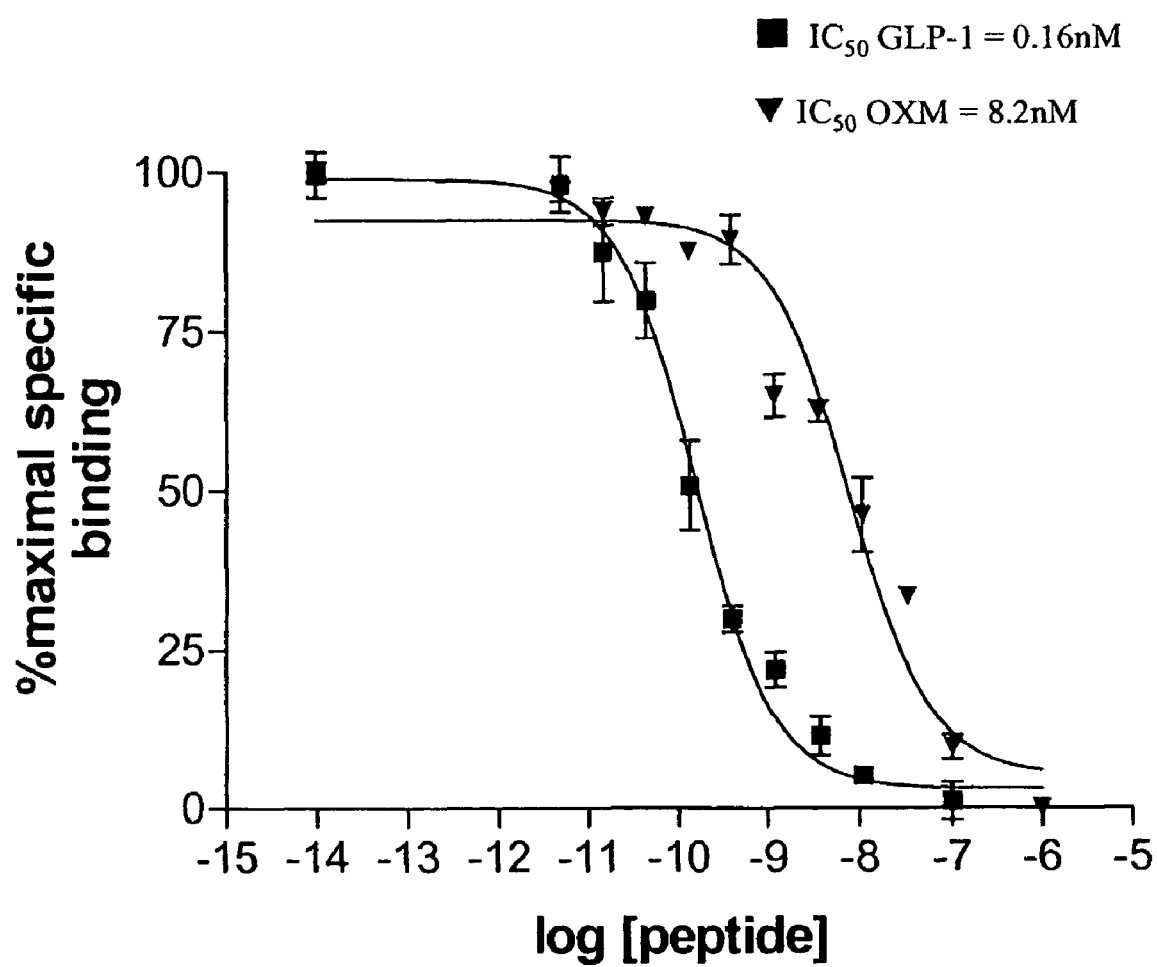

The affinity ($IC_{50}$) of GLP-1 for the GLP-receptor in rat hypothalamic membrane preparations was 0.16 nM (FIG. 5). The affinity of OXM for the GLP-1 receptor in the same membrane preparations was 8.2 nM (FIG. 5), which is approximately 2 orders of magnitude weaker than that of GLP-1.

Discussion.

OXM causes a potent decrease in fasting-induced refeeding when injected both ICV and iPVN. The effect was sustained until 8 h (iPVN) or 4 h (ICV) postinjection. The effect of OXM is approximately of the same magnitude and time course as that of GLP-1 when administered ICV and iPVN at equimolar doses. In addition, OXM inhibits food intake in nonfasted rats at the onset of the dark phase, and at that time they showed no signs of aversive behaviour.

It has been suggested that there is an OXM-specific binding site in gastric mucosa. However, no such binding site has been identified in the CNS. Therefore, it was proposed that OXM mediated its effects via the hypothalamic GLP-IR, as GLP-1 and OXM have similar potency in feeding studies. It has been shown that OXM has a nanomolar affinity for the GLP-IR ($IC_{50}=8.2$ nM). This affinity is approximately 2 orders of magnitude weaker than that of GLP-1 ($IC_{50}=0.16$ nM). Yet despite this reduced affinity for the GLP-1R, OXM reduces food intake to the same magnitude. One explanation for this is that OXM might act through both the GLP-1R and its own receptor in the hypothalamus. Thus, OXM could elicit a response comparable to that of GLP-1 despite its lower affinity for the GLP-IR.

Exendin-(9-39), a fragment of the GLP-1R agonist exendin-4, is a potent and selective antagonist at the GLP-1R. When GLP-1 and exendin-(9-39) are coinjected, the anorectic actions of GLP-1 are blocked. When OXM is coinjected with exendin-(9-39), the anorectic effects of OXM are also completely blocked. This would strengthen the argument that OXM is mediating its effects via the GLP-1R.

We investigated the effects of glicentin, and glucagon after an acute ICV injection in fasted rats. No effect on fasting-induced food intake was seen after the administration of these peptides. In addition, there was no effect of these peptides when they were administered iPVN. When SP-1, the putative minimal active structure of OXM, was injected iPVN, no inhibition of food intake was observed. Therefore the effect seen by OXM is specific.

B—Peripheral Administration of OXM Also Reduces Food intake and Body Weight Gain.

Peptides and Chemicals

OXM was purchased from IAF BioChem Pharma (Laval, Canada). GLP-1 was purchased from Peninsula Laboratories Inc. (St. Helens, UK). Exendin 9-39 was synthesised at Medical Research Council, Hemostasis Unit, Clinical Sciences Centre, Hammersmith Hospital, London, UK using F-moc chemistry on a 396 MPS peptide synthesizer (Advanced ChemTech Inc., Louisville, Ky.) and purified by reverse phase HPLC on a $C_8$ column (Phenomex, Macclesfield, UK), using a gradient of acetonitrile on 0.1% trifluoroacetic acid. Correct molecular weight was confirmed by mass spectrometry. All chemicals were purchases from Merck Eurolab Ltd. (Lutterworth, Leicestershire, UK), unless otherwise stated.

Animals

Adult male Wistar rats (180-200 g) were maintained in individual cages under controlled conditions of temperature (21-23° C.) and light (12 hours light, 12 hours dark) with ad libitum access to standard rat chow (RM1 diet, Special Diet Services UK Ltd., Witham, Essex, UK) and water. All procedures undertaken were approved by the British Home Office Animals (Scientific Procedures) Act 1986 (Project Licenses PPL: 90/1077, 70/5281 and 70/5516).

Intra-arcuate Nucleus Cannulation

Animals had permanent indwelling, unilateral, stainless steel guide cannulae (Plastics One, Roanoke, Va.) stereotactically implanted into the arcuate nucleus of the hypothalamus, using a cannulation protocol using cannulae positioned 3.3 mm posterior to and 0.3 mm lateral to bregma and 9.0 mm below the outer surface of the skull.

Intra-peritoneal (IP) Injections

All IP injections were delivered using a 1 ml syringe and a 25 gauge needle. The maximum volume of injection was 500 µl, and was adjusted according the weight of the individual animal. All peptides were dissolved in saline.

In these studies, the human OXM and human GLP-1 were used with the sequences provided on pages 15 and 16 above.

In Vivo Protocols

1. Investigating the Dose-response Effect of Peripheral Administration of OXM on Food Intake in Fasted Animals:

Animals were fasted for 24 hours prior to the study. During the early light phase (09.00-10.00 hr), rats were given a single IP injection of saline, GLP-1 (30 nmol/kg body weight as a positive control) or OXM (10-300 nmol/kg body weight) (n=12 per group) in a volume of 500 µl. Following the injection, the animals were returned to their home cages and provided with a pre-weighed amount of chow. Food intake was measured 1, 2, 4, 8 and 24 hours post-injection.

2. Investigating the Effect of Peripheral Administration of OXM on Food Intake in Non-fasted Animals During the Dark Phase:

The dark phase is the "normal" feeding time for rats. Therefore, any inhibition of food intake at this time could be considered to be more physiological than alterations to refeeding following a fast. Animals received a single IP injection of saline or OXM (3-100 nmol/kg body weight) (n=12 per group) prior to lights out (18.00-19.00 hr). Food intake was measured 1, 2, 4, 8 and 12 hours post-lights-out.

3. The Effect of Repeated IP Injections of OXM 45 animals were randomised by weight into three groups (n=15 per group): 1) Saline-treated with ad libitum access to food, 2) OXM-treated (50 nmol/kg body weight per injection—a dose based on the previous dose-response experiment) with ad libitum access to food, 3) Saline-treated, but food restricted to the mean light and dark phase food intake of the OXM-treated group. Animals were injected twice daily (07.00 and 18.00 hr) for seven days. Food intake (g), body weight (g) and water intake (ml) were measured daily. On the eighth day, the animals were killed by decapitation. Epididymal white adipose tissue (WAT) and interscapular brown adipose tissue (BAT) were removed and weighed as an assessment of body adiposity.

4. Investigating the Effect of Peripheral Administration of OXM on Gastric Emptying Animals were fasted for 36 hours to ensure that the stomach was empty. During the early light phase (09:00-10:00) were allowed ad libitum access to a pre-weighed amount of standard rat chow for thirty minutes. After that time, the food was removed and reweighed. The animals were then IP injected with saline, OXM (50 nmol/kg body weight) or CCK-8 (15 nmol/kg body weight). Rats were then killed at the same times as those used in the previous feeding studies: 1, 2, 4 or 8 hours post-feeding (n=12 per group per timepoint). The CCK-8 group was used as a positive control for the experiment at the two-hour time-point only. Animals were killed by carbon dioxide asphyxiation. A laparotomy was rapidly performed and the stomach exposed. The pyloric junction was ligated (2.0 Mersilk, Johnson & Johnson, Belgium), followed by ligation of the gastro-oesophogeal junction and the stomach was removed. The gastric contents were then removed, placed in a pre-weighed weighing boat and left to air-dry for 48 hours. Once dry, the contents were weighed and the percentage of the chow ingested during the half-hour re-feeding period remaining in the stomach per rat was then calculated using the following formula:

$$\% \text{ food remaining in the stomach} = \frac{\text{dry weight of stomach content}}{\text{weight of food ingested}} \times 100$$

5. Investigating the Effect of Increasing Doses of Intra-arcuate OXM

Intra-arcuate (Intra-ARC (iARC)) cannulated rats (n=12-15 per group) were randomised by weight into 6 groups. During the early light phase (0900-1000), 24-hour fasted rats received an iARC injection of saline, OXM (0.01, 0.03, 0.1, 0.3 or 1.0 nmoles). Food intake was measured 1, 2, 4, 8 and 24 hours post-injection.

6. Investigating Whether Peripherally Administered OXM is Acting Directly Via Arcuate Nucleus GLP-1 Receptors.

Rats cannulated into the arcuate nucleus were randomised into 6 groups (n=10-12 per group). During the early light phase (0900-1000) 24-hour fasted rats received an iARC injection of saline or exendin$_{9-39}$ (5 nmoles) followed by an IP injection of saline, OXM (30 nmoles/kg body weight) or GLP-1 (30 nmoles/kg body weight) 15 minutes later. The injection details are described in Table 1 below.

TABLE 1

| Group | Intra-ARC injection | IP injection |
|---|---|---|
| 1 | Saline | Saline |
| 2 | Saline | OXM (30 nmoles/kg) |
| 3 | Saline | GLP-1 (30 nmoles/kg) |
| 4 | Exendin 9-39 (5 nmoles) | Saline |
| 5 | Exendin 9-39 (5 nmoles) | OXM (30 nmoles/kg) |
| 6 | Exendin 9-39 (5 nmoles) | GLP-1 (30 nmoles/kg) |

Immunohistochemistry 90 minutes after an IP injection of OXM (50 nmol/kg), CCK (15 nmol/kg) or saline, rats were terminally anaesthetized was transcardially perfused with 0.1 M phosphate buffered saline (PBS) following by 4% PB-formalin (PBF). The brains were removed and post-fixed overnight in PBF and then transferred to PB-sucrose (20% w/v) overnight. 40 μm coronal sections of brain and brainstem were cut on a freezing microtome and stained for fos-like immunoreactivity (FLI) by the avitin-biotin-peroxidase method. The sections were then mounted on poly-L-lysine-coated slides, dehydrated in increasing concentrations of ethanol (50-100%), delipidated in xylene and coverslipped using DPX mountant. Slides were examined for FLI-positive nuclei using a light microscope (Nikon Eclipse E-800) and images captured using a microimager (Xillix MicroImager). The numbers of FLI-positive nuclei in the hypothalamus and brainstem were counted by an independent member of the research team who was blinded to the experimental groups. The average number of FLI-positive nuclei per section was calculated and expressed as an integer for each animal.

Hypothalamic Explant Static Incubation

A static incubation system was. Male Wistar rats were killed by decapitation and the whole brain removed immediately. The brain was mounted, ventral surface uppermost, and placed in a vibrating microtome (Microfield Scientific Ltd., Dartmouth, UK). A 1.7 mm slice was taken from the basal hypothalamus, blocked lateral to the Circle of Willis and incubated in chambers containing 1 ml of artificial cerebrospinal fluid which was equilibrated with 95% $O_2$ and 5% $CO_2$. The hypothalamic slice encompassed the medial preoptic area, PVN (paraventricular hypothalamic nucleus), dorsomedial nucleus, ventromedial nucleus, lateral hypothalamus and ARC. The tubes were placed on a platform in a water bath maintained at 37 C. After an initial 2-hour equilibration period, each explant was incubated for 45 minutes in 600 μl aCSF (basal period) before being challenged with a test period. OXM, 100 nM was used as a dose representing a concentration ten times that of its $IC_{50}$ for the GLP-1 receptor. The viability of the tissue was confirmed by a final 45-minute exposure to aCSF containing 56 mM KCl. At the end of each experimental period, the aCSF was removed and stored at −20° C. until measurement of αMSH-immunoreactivity by radioimmunoassay.

Radioimmunassay to Measure αMSH-IR

Alpha-MSH was measured using an in-house radioimmunoassay, developed using an antibody from Chemicon International Inc.

Statistical Analysis

Data from IP and iARC feeding studies were analyzed by ANOVA with post-hoc LSD (least significant difference) test. Fat pad weights from different treatment groups were analyzed using an unpaired t test. Data from the hypothalamic explant incubation study, in which each explant was compared with its own basal period, were analyzed by paired t test. In all cases P<0.05 was considered to be statistically significant.

Results

Figure 6A:
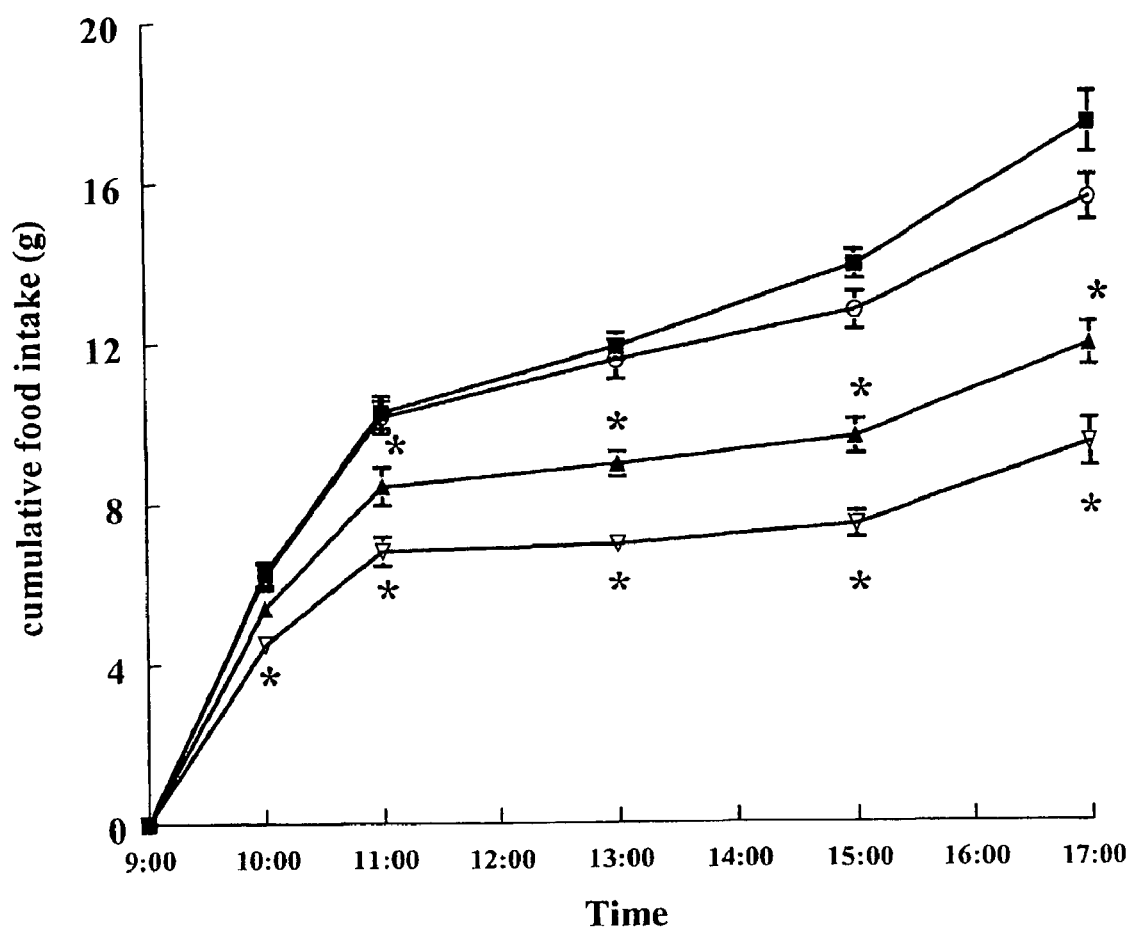

1. The Effect of Peripheral Administration of OXM in Fasted Animals:

Intraperitoneal administration of OXM (100 nmol/kg and 300 nmol/kg) caused a significant inhibition in refeeding in 24-hour fasted animals one hour post-injection, compared with saline controls (1 hour: OXM 100 nmol/kg, 5.4±0.2 g (P<0.05), 300 nmol/kg, 4.5±0.2 g (P<0.05) vs. saline, 6.3±0.2 g). The reduction in food intake caused by 100 nmol/kg was sustained until 8 hours post-injection. However, the highest dose of OXM (300 nmol/kg) continued to significantly inhibited food intake 24 hours post-injection (24 hours: OXM, 300 nmol/kg, 9.5±0.6 g vs. saline, 17.5±0.7 g; P<0.05) (FIG. 6a). The 30 nmol/kg and 10 nmol/kg failed to alter food intake at any time-point investigated.

Figure 6B:
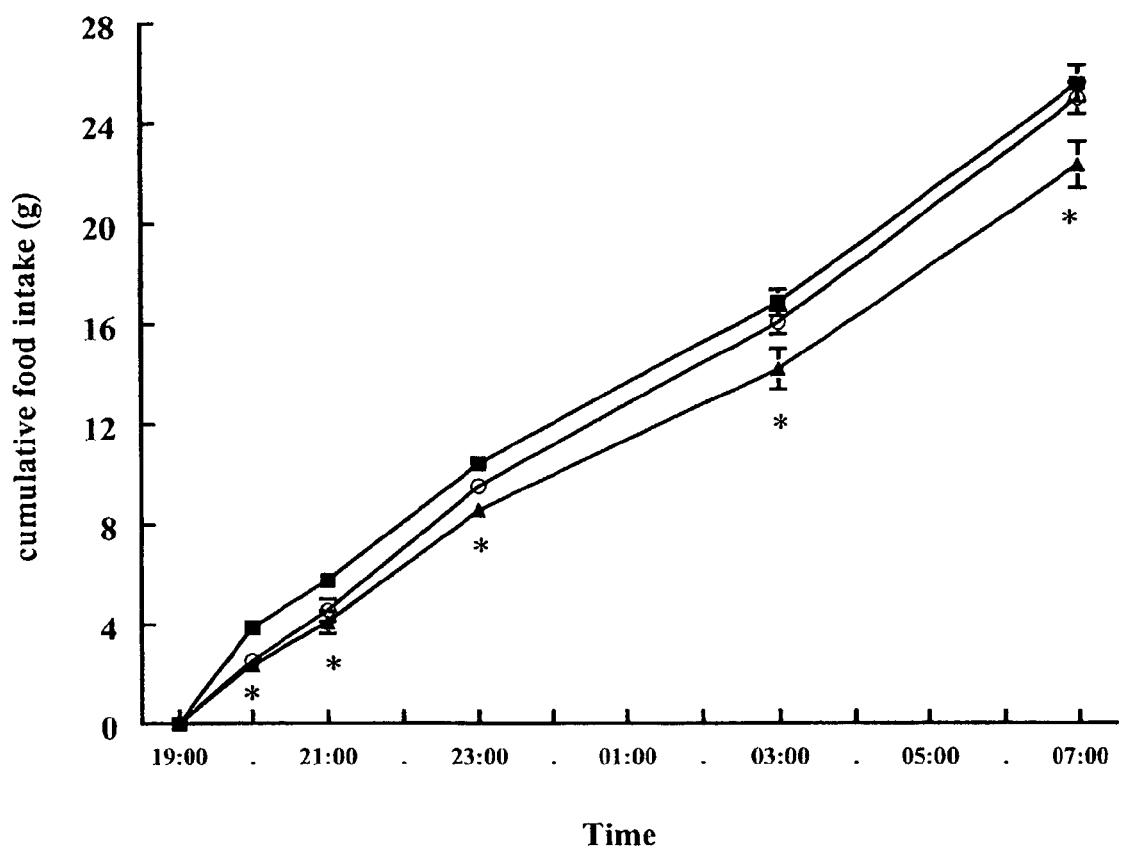

2. The Effect of Peripheral Administration of OXM in Non-fasted Animals on Dark Phase Food Intake:

OXM, 3 and 10 nmol/kg, failed to affect food intake at any time-point investigated in nocturnally feeding rats injected immediately prior to the dark phase. However, OXM, 30 nmol/kg, significantly inhibited food intake until 2 hours post-injection (2 hours: OXM, 30 nmol/kg, 4.5±0.4 g vs. saline, 5.8±0.4 g; P<0.05). Food intake was reduced 4 hours post-injection, but this was not significant. OXM, 100 nmol/kg, significantly inhibited food intake throughout the dark phase (8 hours: OXM, 100 nmol/kg, 14.1±0.8 g vs. saline, 16.9±0.5 g; P<0.05) (FIG. 6b).

3. The Effect of Repeated IP Administration of OXM

Figure 7A:
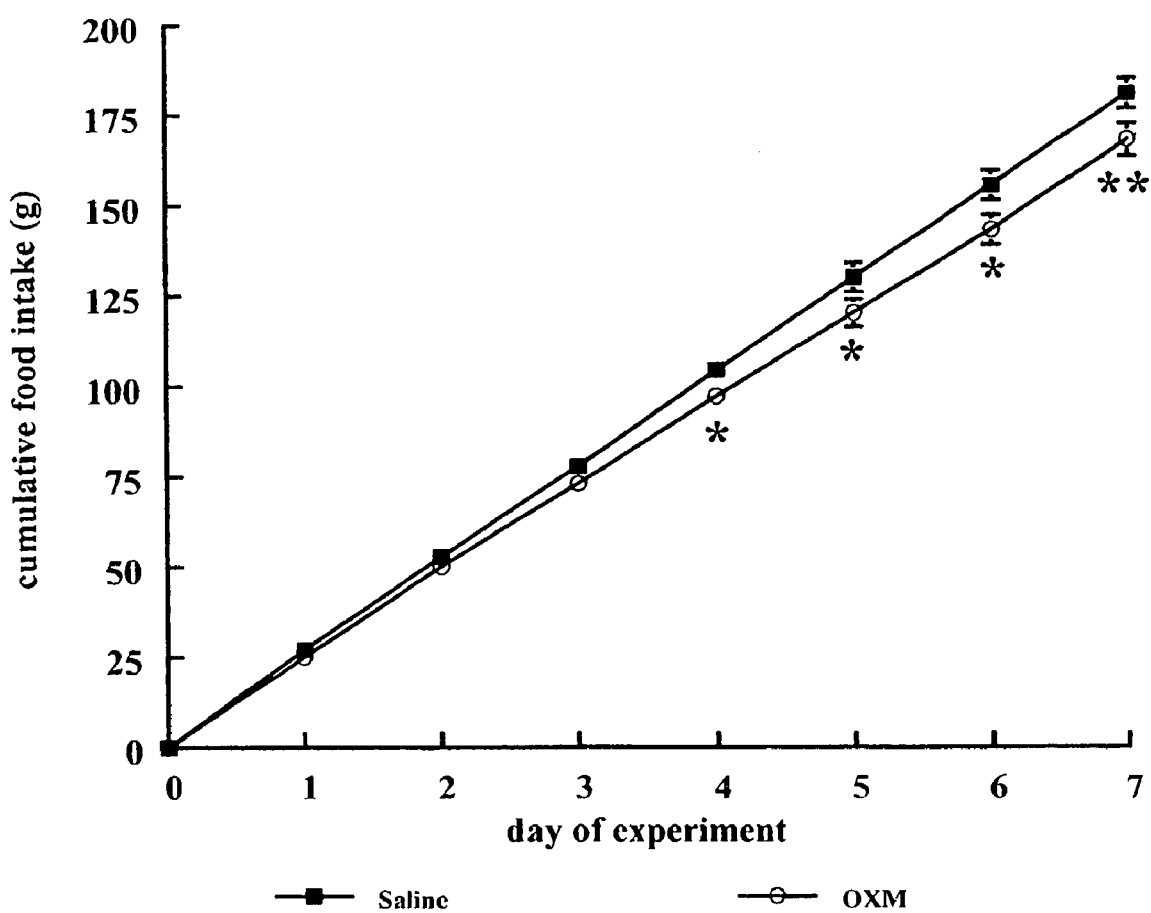
FIG. 7 illustrates the effect of twice daily IP injections of OXM (50 nmol/kg) or saline for seven days on a) cumulative food intake (g); and b) body weight gain (g). *P<0.05, P<0.01, *P<0.005 vs. saline.
Figure 7B:
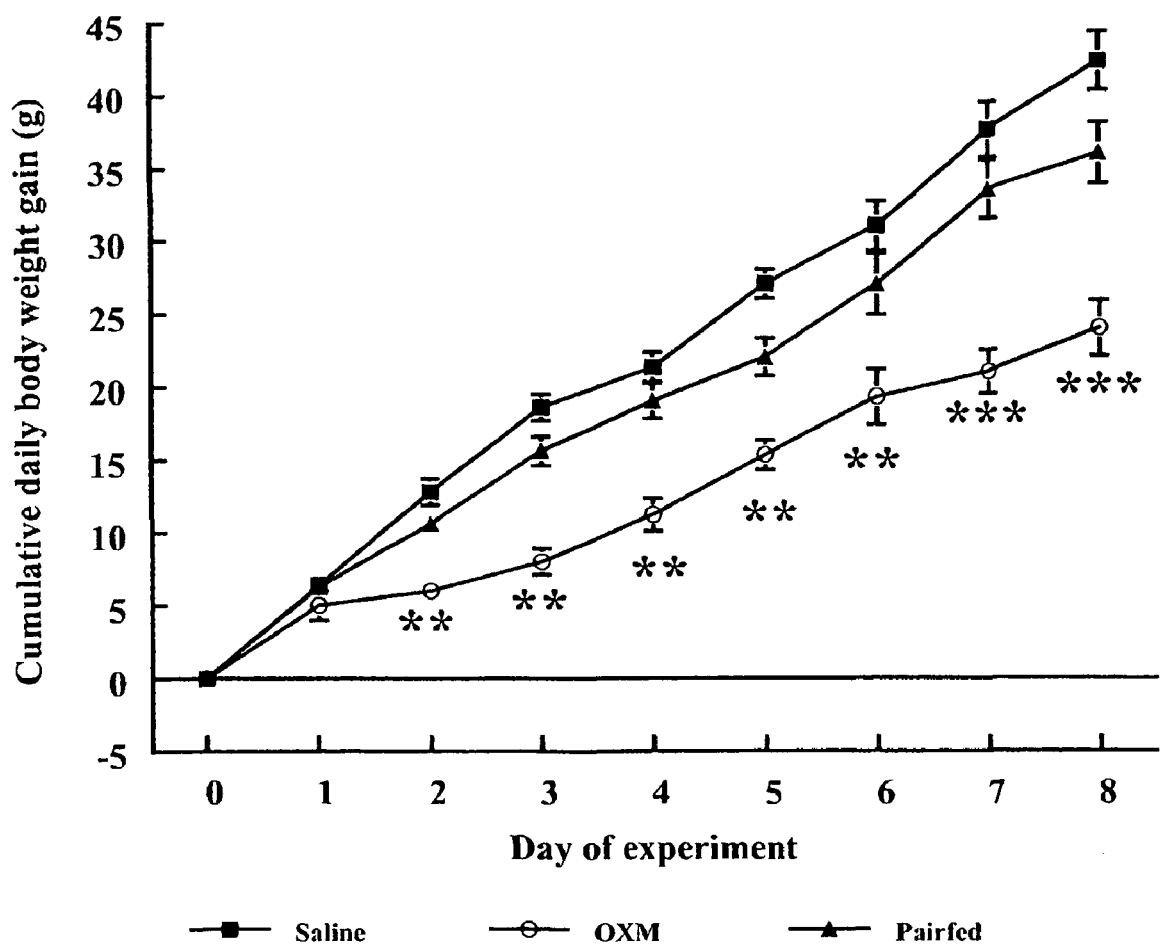

Twice-daily IP injections of OXM (50 nmol/kg) for seven days caused a significant decrease in cumulative daily food intake, compare with saline-treated control animals (Cumulative food intake day 7: OXM, 50 nmol/kg, 168 ±4.6 g vs. saline, 180±4.3 g; P<0.01) (FIG. 7a). Furthermore, OXM-treated animals gained weight significantly more slowly than saline controls (cumulative weight gain day 7: OXM, 50 nmol/kg, 21.0±1.5 g vs. saline, 37.6±1.9 g; P<0.005). Moreover, the food restricted "pair fed" animals did not gain weight as slowly as OXM-treated animals, despite receiving the same food intake (Day 7: pair fed, 33.5±2.0 g; P=NS vs. saline (ad libitum fed), P<0.05 vs. OXM) (FIG. 7b). In addition, chronic OXM caused a decrease in adiposity that was not seen in saline-injected pair fed animals (Table 2). Water intake was significantly reduced in OXM-treated animals on days 1 and 2 of the experiment (Day 1: OXM, 24.1±1.28 ml vs. saline, 28.1±1.33 ml; P<0.05). On subsequent days, there was an increase in daily water intake compared with saline-treated animals (days 3-6). However, by day 7, there was no difference in water intake between saline and OXM-treated groups (not shown).

TABLE 2

The effect of twice-daily IP administration of saline or OXM (50 nmol/kg) for seven days on the weight of epididymal WAT and interscapular BAT in food restricted and ad libitum fed rats.

| Tissue/hormone | Saline | OXM | Pairfed |
|---|---|---|---|
| WAT | 0.69 ± 0.02 | 0.51 ± 0.01[a] | 0.61 ± 0.02[b] |
| BAT | 0.16 ± 0.01 | 0.12 ± 0.01[a] | 0.15 ± 0.01[b] |

Figure 8:
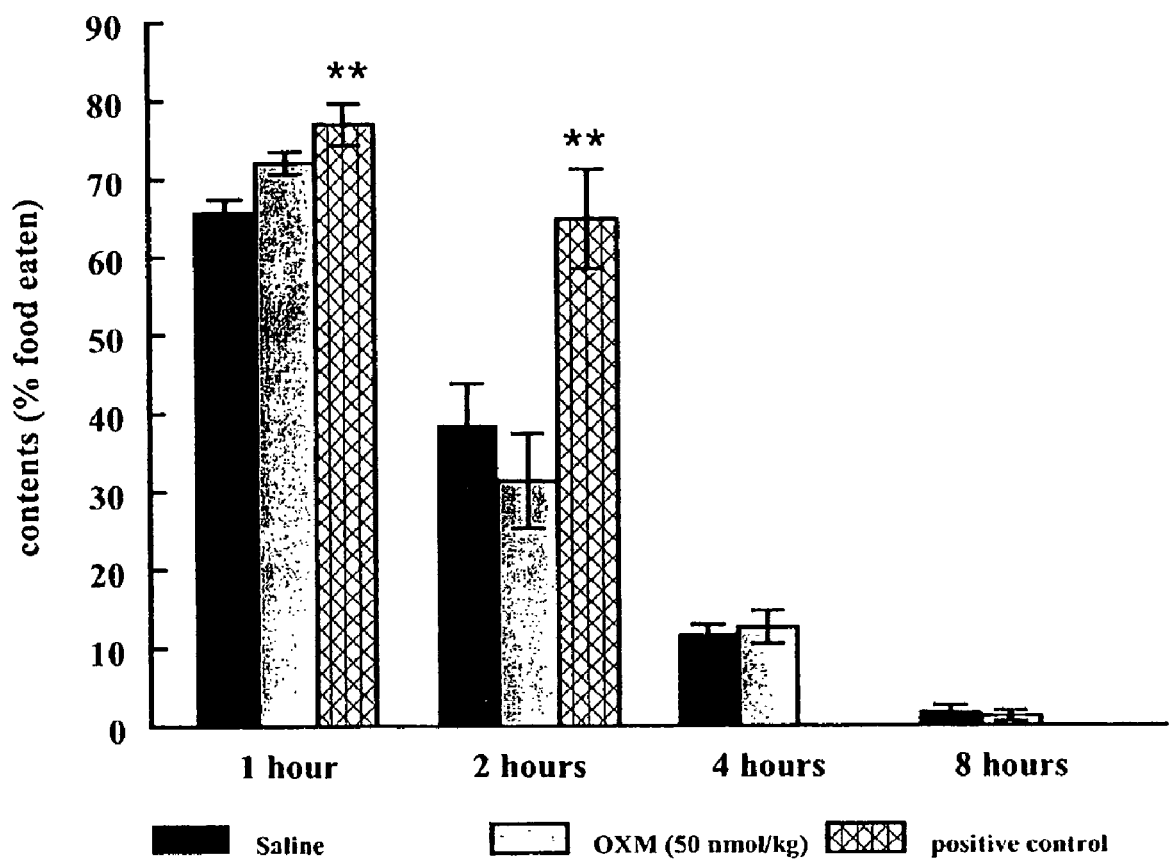
FIG. 8 illustrates the effect of IP OXM (50 nmol/kg), saline or a positive control (1 hour=GLP-1 (50 nmol/kg); 2 hours =CCK (15 nmol/kg)) on gastric emptying in 36-hour fasted rats. Contents (dry weight) of the stomach were expressed as a percentage of the food intake during the 30-minute feeding period. **P<0.01 vs. saline.

4. The Role of Delayed Gastric Emptying on the Anorectic Effect of OXM:

One hour after food was presented to the 36-hour fasted rats, the dry weight of the contents of the stomachs (as a percentage of the food consumed during the 30 minute feeding period) of GLP-1-treated animals were significantly greater than that of saline-treated animals (1 hour: GLP-1, 50 nmol/kg, 76.9±2.7 g vs. saline, 65.8±1.6 g; P<0.01), suggesting that GLP-1 caused a significant decrease in gastric emptying. The contents of the stomachs of OXM-treated animals were greater than those of the saline treated controls, although this was not statistically significant (1 hour: OXM, 50 nmol/ kg, 72.0±1.4 g vs. saline 65.8±1.6 g; P=0.07). Two hours post-feed, OXM did not affect the contents of the stomach, compared with saline-treated animals. However, animals injected with the positive control for this time-point, CCK (15 nmol/kg), had significantly greater stomach content (2 hours: CCK, 15 nmol/kg, 64.7±6.4 g vs. saline, 38.5 g; P<0.01), suggesting that CCK caused a significant decrease in the rate of gastric emptying. There was no effect of OXM on the contents of the stomach, compared with saline-treated animals, at 4 or 8 hours post-feed (FIG. 8).

Figure 9:
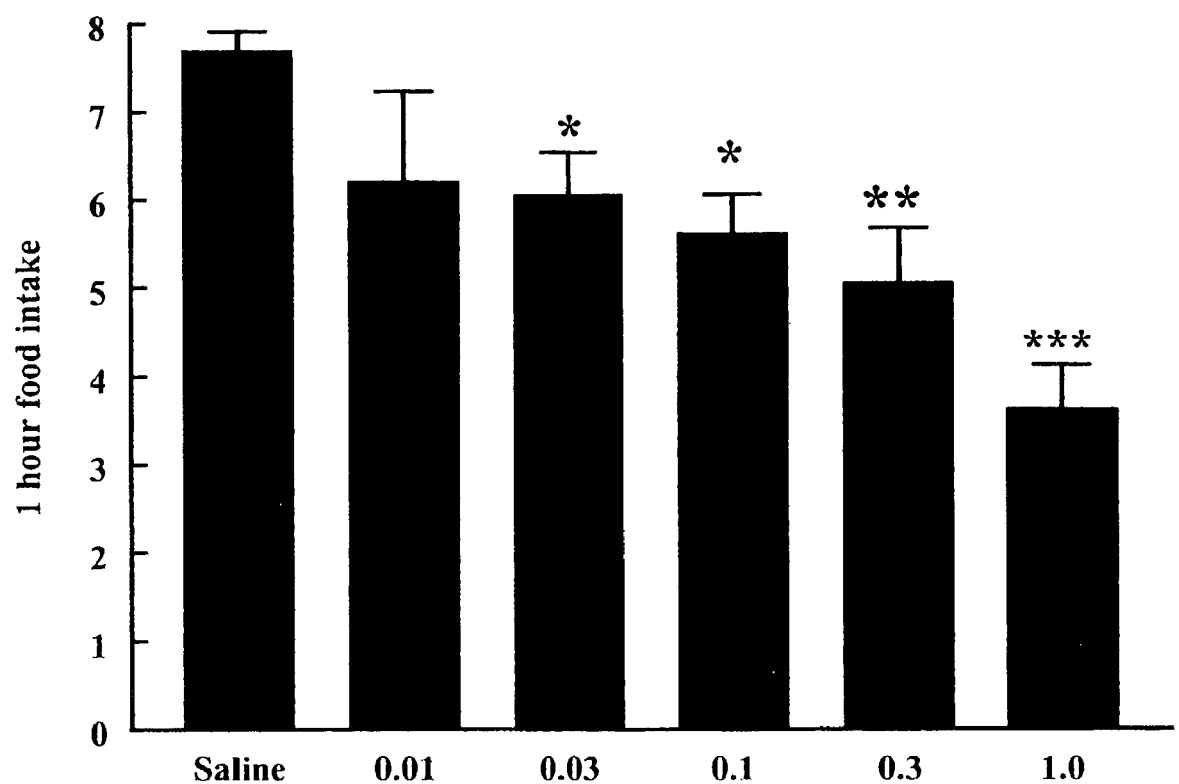
FIG. 9 illustrates the effect of increasing doses of OXM (0.01-1.0 nmole) on 1 hour food intake when administered into the arcuate nucleus of 24-hour fasted rats. *P<0.05, P<0.01, *P<0.05 vs. saline.

5. Investigating the Effect of Increasing Doses of OXM Injected Intra-arcuate Nucleus Food intake was significantly inhibited by all doses (except 0.01 nmoles) of OXM administered iARC during the $1^{st}$ hour of re-feeding following a 24-hour fast (1 hour: OXM 0.03 nmoles, 6.1±0.5 g (P<0.05); 0.1 nmoles, 5.6±0.4 g (P<0.05); 0.3 nmoles, 5.1±0.6 g (P<0.01); 1.0 nmole, 3.6±0.5 g (P<0.005) all vs. saline, 7.7±0.2 g) (FIG. 9). OXM 0.3 and 1.0 nmoles continued to significantly inhibit food intake until 8 hours post-injection. Twenty-four hours post-injection, food intake was inhibited by OXM 1.0 nmoles, although this was not significant (24 hours: OXM, 1.0 nmole, 37.8±3.0 g vs. saline, 40.8±1.6 g; P=NS).

6. Investigating Whether Peripherally Administered OXM is Acting Via Arcuate Nucleus GLP-1 Receptors Intraperitoneal administration of both GLP-1 (30 nmol/kg) and OXM (30 nmol/kg) caused a significant inhibition of food intake one hour into the dark phase (1 hour: GLP-1, 5.0±0.6 g, OXM, 5.1±0.4 g vs. saline, 9.2±0.3 g). However, the anorexia caused by IP administration of OXM was blocked by prior administration of the GLP-1 receptor antagonist, exendin 9-39 (300 nmol/kg), injected directly into the ARC (Table 3 & FIG. 10). Inhibition of food intake by IP GLP-1 was not affected by prior iARC administration of exendin 9-39.

TABLE 3

The effect of iARC administration of exendin 9-39 (5 nmoles) or saline injected 15 minutes prior to IP administration of OXM (30 nmol/kg), GLP-1 (30 nmol/kg) or saline on 1 hour food intake (g). (S = saline, G = GLP-1 (30 nmol/kg), Ox = OXM (30 nmol/kg), Ex = exendin 9-39 (5 nmoles)).

| Peptide | Food intake (g) | S.E.M. |
|---|---|---|
| Saline/saline | 9.2 | 0.3 |
| Saline/GLP-1 | 5.0 | 0.6 |
| Exendin 9-39/GLP-1 | 5.0 | 0.3 |
| Saline/OXM | 5.1 | 0.4 |
| Exendin 9-39/OXM | 9.4 | 0.4 |
| Exendin 9-39/saline | 9.0 | 0.3 |

7. Mapping the Expression of FLI in the Hypothalamus in Response IP OXM:

After IP OXM administration (50 nmol/kg) dense staining of FLI was found almost exclusively in the hypothalamic arcuate nucleus (FIG. 11a). No other hypothalamic nuclei (PVN (paraventricular hypothalamic nucleus), DMH (dorsomedial hypothalamic nucleus), VMH (ventromedial hypothalamic nucleus)) demonstrated specific c-fos staining.

In the brainstem, IP CCK (15 nmol/kg) caused dense staining of FLI, most notably in the NTS (nucleus tractus solitarius) and the area postrema (FIG. 6b). However, neither IP saline nor IP OXM (50 nmol/kg) caused a specific increase in c-fos expression in the same brainstem nuclei investigated (FIG. 11b).

8. Changes in Alpha-MSH Release from Hypothalamic Explants When Incubated with OXM Incubating OXM (100 nM) was hypothalamic explants caused a significant increase in the release of α-MSH, compared with basal release (α-MSH: OXM, 100 nM, 4.1±0.6 fmol/explant vs. 2.6±0.5 fmol/explant; P<0.005). Explant viability was assessed by incubation with 56 mM KCl, and viability was confirmed in >80% of explants. Those explants that were not viable were excluded from the analysis.

Discussion

Peripheral administration of OXM causes a reduction in food intake in rats. This was seen following a fast in the light phase and during the nocturnal feeding phase. The anorectic effect was potent and sustained for periods up to 24 hours. Twice-daily IP administration of OXM for seven days caused a reduction in daily food intake compared with those treated with saline, with no tachyphylaxis. Animals treated with OXM gained significantly less weight than pair fed animals, despite the two groups receiving identical daily caloric intake. Intraperitoneal administration of OXM did transiently reduce water intake although this was not sustained, suggesting that the reduction in the rate of body weight gain was not due to dehydration.

On conclusion of the chronic study, epididymal WAT and interscapular BAT were removed and weighed. It was found that there was a reduction in the weights of all fat pads in OXM-treated animals compared with pair-fed animals, despite identical food intake. Therefore it appears that peripheral OXM administration is also affecting other metabolic parameters.

A major contributor to satiety is delayed gastric emptying via vagally-mediated mechanism that leads to brainstem activation. Both GLP-1 and OXM are potent inhibitors of gastric emptying in rodents and humans and in the case of GLP-1, this is thought to be the dominant mechanism through which it promotes satiety. We hypothesized that OXM was acting in the same way, and that its effects on gastric emptying were the cause of sustained anorexia. However, although peripheral administration of OXM led to a slight delay in gastric emptying in the first hour after the re-introduction of food, this was non-significant and the effect was short-lived. This suggested that OXM does slow gastric emptying, but it is not likely to be responsible for the robust and sustained inhibition of food intake.

We report here that peripheral administration of OXM increases FLI in almost exclusively in the ARC. Furthermore, we found that incubating hypothalamic explant with OXM caused a significant increase in the release of the POMC (pro-opiomelanocortin)-derived product, aMSH from hypothalamic explants. IP OXM not affect the expression of FLI in the NTS and AP—areas known to be important in integrating vagally mediated information, further strengthening the notion that OXM is not acting via these pathways.

It is thought that nuclei in the brainstem are the primary site of GLP-1 action, and information is subsequently relayed to the hypothalamic PVN, where its anorectic effects are mediated. Direct injection of OXM into the ARC, even at very low doses caused a robust and sustained inhibition of food intake, further supporting the hypothesis that that the ARC is the site of the actions of OXM. Anorectic effects caused by peripheral administration of OXM were blocked by prior administration of exendin$_{9-39}$ into the ARC. Interestingly, however, the anorectic actions of peripherally administered GLP-1 were not. This finding strongly indicates that OXM is acting via GLP-1 receptors in the ARC. In addition, it has identified distinct pathways which mediate the actions of GLP-1 and OXM.

Taken together, these data demonstrate that OXM is potentially important in both long and short-term regulation of food intake and body weight maintenance. Rather than reducing appetite via "traditional" satiety pathways, involving slowing of gastric emptying and activation of brainstem nuclei, circulating OXM is mediating its anorectic effects via direct interaction with the ARC, potentially by activating POMC (pro-opiomelanocortin) neurons within the nucleus. Therefore, OXM may be useful in the treatment or prevention of excess weight such as obesity in mammals, and further represents a novel target for the development of therapeutic agents in the treatment of excess weight such as obesity in mammals.

The invention claimed is:

1. A method for the treatment or management of excess weight in a mammal in need thereof, comprising peripherally administering to said mammal oxyntomodulin comprising the amino acid sequence of SEQ ID NO:1, 2 or 3, or a pharmaceutically acceptable salt thereof, in an amount effective to treat or manage the excess weight in said mammal.

2. The method of claim 1, wherein said mammal is a human.

3. The method of claim 1, wherein said excess weight is a symptom of obesity.

4. The method of claim 1, wherein cosmetic weight loss is achieved.

5. The method of claim 1, wherein said oxyntomodulin is administered to said mammal by parenteral, intraperitoneal, or subcutaneous administration.

6. A method for the treatment or management of obesity in a mammal in need thereof, comprising administering to said mammal oxyntomodulin comprising the amino acid sequence of SEQ ID NO:1, 2 or 3, or a pharmaceutically acceptable salt thereof, in an amount effective to treat or manage obesity in said mammal.

7. The method of claim 6, wherein said mammal is a human.

8. The method of claim 6, wherein said excess weight is a symptom of obesity.

9. The method of claim 6, wherein cosmetic weight loss is achieved.

10. The method of claim 6, wherein said oxyntomodulin is administered to said mammal by parenteral, intraperitoneal, or subcutaneous administration.

11. The method of claim 6, wherein the oxyntomodulin is administered by peripheral administration.

12. The method of claim 1 or 6, wherein said oxyntomodulin is administered to said mammal by inhalation or by buccal, sublingual or nasal administration.

13. The method of claim 1 or 6, wherein said oxyntomodulin is administered to said mammal in the presence of a metal.

14. The method of claim 13, wherein the metal is selected from the group consisting of calcium, magnesium, manganese and zinc.

15. The method of claim 1 or 6, wherein said oxyntomodulin comprises the amino acid sequence of SEQ ID NO:1.

16. The method of claim 1 or 6, wherein said oxyntomodulin comprises the amino acid sequence of SEQ ID NO:2.

17. The method of claim 1 or 6, wherein said oxyntomodulin comprises the amino acid sequence of SEQ ID NO:3.

18. The method of claim 1 or 6, wherein said oxyntomodulin is human *oxyntomodulin*.

* * * * *